United States Patent [19]

Kimura et al.

[11] Patent Number: 5,702,352

[45] Date of Patent: Dec. 30, 1997

[54] TOOLS AND METHOD FOR MANIPULATING ORGANS IN HUMAN BODY

[75] Inventors: Shuichi Kimura, Hino; Tsuyoshi Tsukagoshi, Fuchu, both of Japan

[73] Assignee: Olympus Optical Co., Ltd., Tokyo, Japan

[21] Appl. No.: 528,954

[22] Filed: Sep. 15, 1995

[30] Foreign Application Priority Data

Sep. 26, 1994 [JP] Japan .................................. 6-229293
Jun. 14, 1995 [JP] Japan .................................. 7-147391

[51] Int. Cl.$^6$ ............................................. A61B 17/00
[52] U.S. Cl. .......................... 600/201; 600/235; 606/41
[58] Field of Search .............................. 604/95, 21, 158, 604/22, 164; 606/108, 41, 151, 213; 600/201–246

[56] References Cited

U.S. PATENT DOCUMENTS

| Re. 34,021 | 8/1992 | Mueller et al. . |
|---|---|---|
| 5,041,129 | 8/1991 | Hayhurst et al. . |
| 5,074,846 | 12/1991 | Clegg et al. . |
| 5,112,310 | 5/1992 | Grobe . |
| 5,123,914 | 6/1992 | Cope . |
| 5,213,575 | 5/1993 | Scotti . |
| 5,429,636 | 7/1995 | Shikhman et al. . |
| 5,456,246 | 10/1995 | Schmieding et al. . |
| 5,531,759 | 7/1996 | Kensey et al. . |

FOREIGN PATENT DOCUMENTS

| 0651929 | 7/1993 | Australia ................................ 606/213 |
|---|---|---|
| 4-226676 | 8/1992 | Japan . |
| 1319834 | 6/1987 | U.S.S.R. . |

Primary Examiner—Mark Bockelman
Attorney, Agent, or Firm—Frishauf, Holtz, Goodman, Langer & Chick

[57] ABSTRACT

A tool for manipulating tissue includes a penetration needle adapted to be stuck into a body cavity of a patient. A pulling device is insertable into a hollow portion of the penetration needle so as to be positioned in the body cavity of the patient when the penetration needle is stuck therein. The pulling device is adapted to pull tissue in the body cavity and the penetration needle is adapted to be removed from the body cavity after the pulling device is positioned therein. A manipulating device having a hollow portion through which the pulling device can be passed is adapted to be guided over the pulling device to be inserted into the body cavity of the patient after the penetration needle is removed therefrom. The manipulating device is adapted to be positionally fixed relative to the pulling device and to be operable together with the pulling device to move the pulled tissue in a desired direction and to hold the pulled tissue at a desired position.

28 Claims, 14 Drawing Sheets

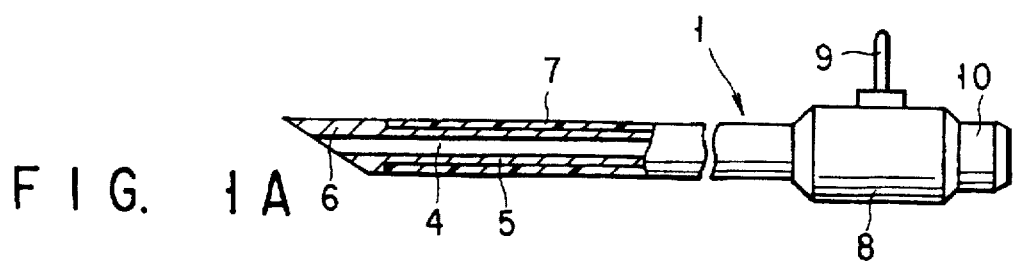
FIG. 1A
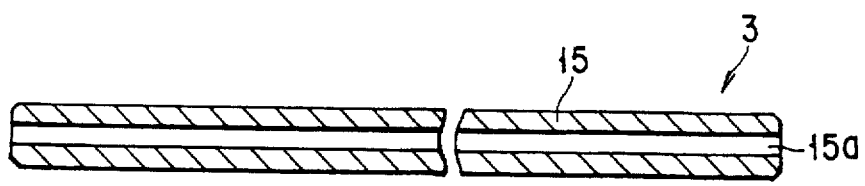
FIG. 1B
FIG. 1C
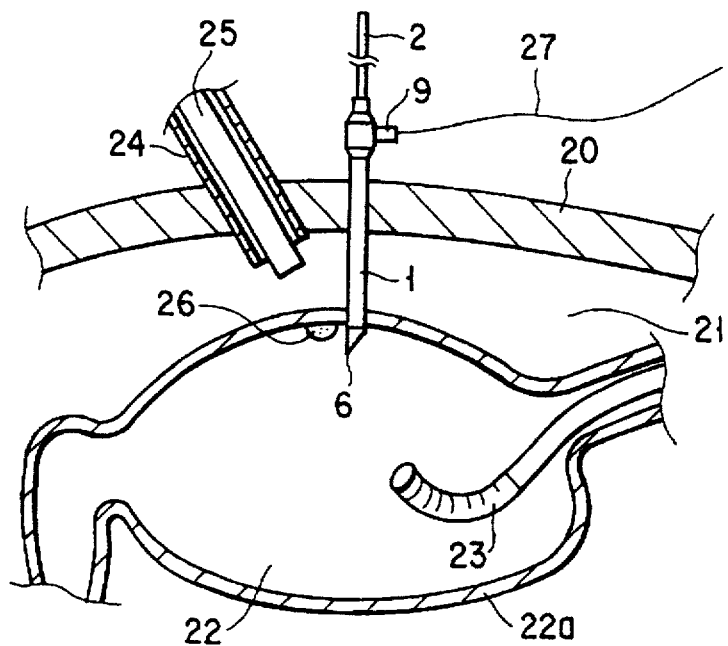
FIG. 2

FIG. 24
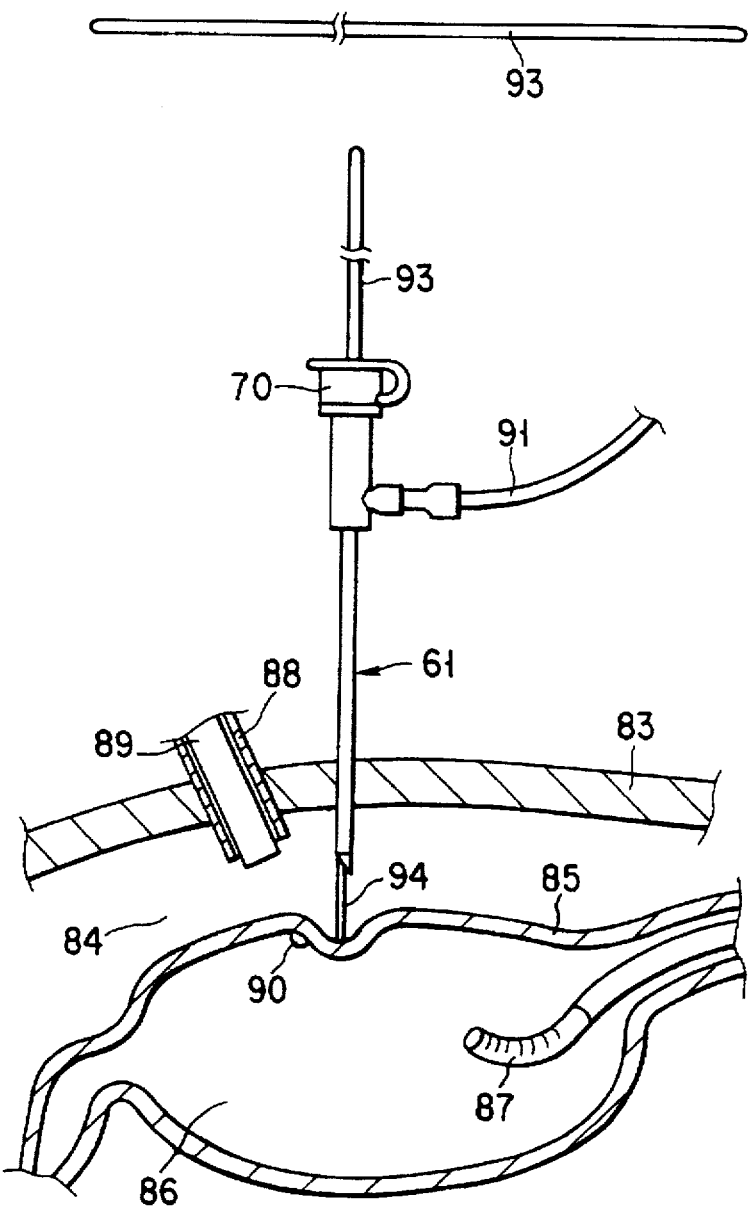
FIG. 25
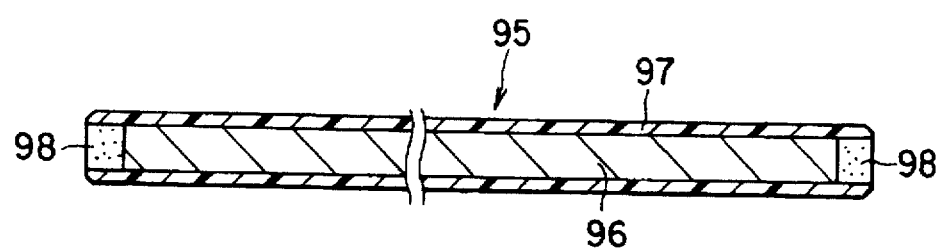
FIG. 26

TOOLS AND METHOD FOR MANIPULATING ORGANS IN HUMAN BODY

BACKGROUND OF THE INVENTION

1. Field of the Invention

The present invention relates to a tool used to manipulate or hang up an organ such as the stomach or intestines in the human body when a surgical operation is performed, for example, through a laparoscope. The present invention also relates to a method of manipulating the tool.

2. Description of the Related Art

When an organ such as the stomach or intestines in human body is to be surgically operated on through a laparoscope, i.e. when an affected part such as cancerous cells caused at a part of the walls of the stomach, for example, is to be cut off, the wall around the affected part is kept hung-up by the hang-up tool, which has been inserted into the body cavity through the belly wall. The affected area is then cut off by a linear cutter inserted into the body cavity through a trocar which has been stuck into the belly wall at a different position.

A hang-up tool conventionally used in this case is well-known from Jpn. Pat. Appln. KOKAI Publication No. Hei 4-226676, U.S. Pat. Nos. 5,112,310 and 5,123,914, for example. In the case where the surgical operation is conducted through an endoscope using such a hang-up tool, the partial cut-off of the stomach is usually carried out, following the below-mentioned steps while keeping the affected part of the stomach hung up.

1) The endoscope is inserted into the stomach of an patient and the stomach is then swelled by a air supply means of the endoscope;

2) Light shot from the endoscope in the stomach is confirmed from the side of the belly wall by an laparoscope inserted into the body cavity of the patient at a position different from the endoscope, and a penetration or centesis needle is stuck into that part thus confirmed and then introduced into the stomach through the belly wall and the stomach (or front) wall;

3) A hang-up tool to which a T-fastener having a horizontal rod at the front end of a thread is connected and which has been disclosed in Jpn. Pat. Appln. KOKAI Publication No. Hei 4-226676, for example, is previously arranged in the penetration needle. The T-fastener is detached from the penetration needle, which is then removed leaving the T-fastener and the thread in the stomach. The T-fastener is then engaged with the stomach wall to hang it up from inside the stomach;

4) Air in the stomach is exhausted Outside to some extent and the thread is pulled from outside the belly wall (or human body). That part of the stomach which is to be cut off is thus hung up by the hang-up tool;

5) A surgical operating linear cutter is inserted into the body cavity under the endoscope, passing through a trocar which is still left inserted into the belly wall at the different position; and 6) That part of the stomach which is left hung up to be cut off is pulled between a cartridge and an anvil of the linear cutter and then cut off while manipulating the linear cutter.

In the case where a part of the stomach is hung up and then cut off by the above-described conventional technique, however, the following problems are caused. When the penetration needle is stuck into the stomach at the step 2), it is difficult for the needle to cut up the mucous membrane on the front wall of the stomach by its tip because the mucous membrane extends. It is when the mucous membrane extends to almost reach the rear wall of the stomach that the needle can cut. The needle is thus made free into the stomach at the instant when the mucous membrane on the front wall of the stomach extends to its limit and thus the needle can damage the rear wall of the stomach by its front tip.

Further, the needle can be stuck into the front wall of the stomach while confirming whether or not any blood vessel is present there under the light shot from the endoscope. Blood vessels in the rear wall of the stomach, however, cannot be confirmed. Therefore, there is the possibility that the needle may be stuck into one of them. In addition, there is the possibility that the needle may be stuck into blood vessels and organs behind the rear wall of the stomach after penetrating it.

Furthermore, the thread is naturally soft. When the affected part of the stomach is hung up at the step 4), therefore, the direction in which it is hung up is determined by two points of those positions at which the needle is stuck into the belly wall and the stomach. In the case of the conventional hang-up tool, therefore, only the amount of the stomach wall hung up can be changed no matter how the thread may be manipulated. It is therefore difficult to accurately pull that part of the stomach, which is to be cut off, between the anvil and the cartridge of the linear cutter. The work of accurately positioning the cut-off part of the stomach between the anvil and the cartridge of the linear cutter is thus carried out by manipulating the cutter. This is troublesome and operation time becomes long accordingly. In addition, it is difficult to accurately cut off the target portion of the stomach along a cut-off line and this can undesirably result in the cutting off of a normal part of the stomach.

SUMMARY OF THE INVENTION

The present invention is therefore intended to eliminate the above-mentioned drawbacks.

Accordingly, the object of the present invention is to provide tool and method capable of sticking the tool into an organ in the human body to more easily manipulate or hang up an intended part of the organ.

The object of the present invention can be achieved by a tool for manipulating an organ in the human body of a patient, the tool comprising a centesis or penetration hollow needle stuck into the human body of the patient; means arranged in the hollow penetration needle and inserted together with the needle into the human body of the patient to pull the organ; and means having a hollow into which the pulling means can be freely inserted, and stuck into the human body of the patient, instead of the penetration needle, to manipulate the organ in the human body, while keeping its movement fixed relative to the pulling means.

When the wall of the stomach is to be hung up, for example, the penetration needle with the pulling means housed therein is stuck into the belly wall and then into that part of the stomach wall which is around a part confirmed to be affected. Upon doing this, high frequency current is caused to flow to the front tip of the penetration needle, if necessary. The needle can be thus stuck into the stomach wall while applying high frequency cutting to it.

Only the penetration needle is pulled out of the belly wall and the manipulator means is then fitted onto the pulling means, which is still left in those holes of the belly and stomach walls opened by the penetration needle, and inserted into the body cavity. The stomach wall is sandwiched and fixed between the manipulator and the pulling means. An assembly of the manipulator and the pulling means is then operated under this state to change the stomach wall into a desired shape.

According to the present invention, the tool can be more easily stuck into an organ in the human body to hang up an intended part of the organ. When the removed part of an organ is to be conducted by surgical operation through an endoscope, therefore, an intended part of the organ can be more reliably cut off. In addition, the operation can be conducted for a shorter time and with a higher safety.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 1A is a side view showing a centesis or penetration needle of the hang-up tool according to a first embodiment of the present invention, said needle being partly sectioned;

FIG. 1B is a side view showing a pulling member of the hang-up tool;

FIG. 1C is a side view showing a sheath of the hang-up tool;

FIG. 2 shows the penetration needle stuck into belly and stomach walls;

FIG. 24 is a side view showing a guide rod of the hang-up tool according to a twelfth embodiment of the present invention;

FIG. 25 is a view intended to explain how the guide rod is used;

FIG. 26 is a vertically-sectioned view showing a guide rod of the hang-up tool according to a thirteenth embodiment of the present invention;

DETAILED DESCRIPTION OF THE PREFERRED EMBODIMENTS

Figure 3:
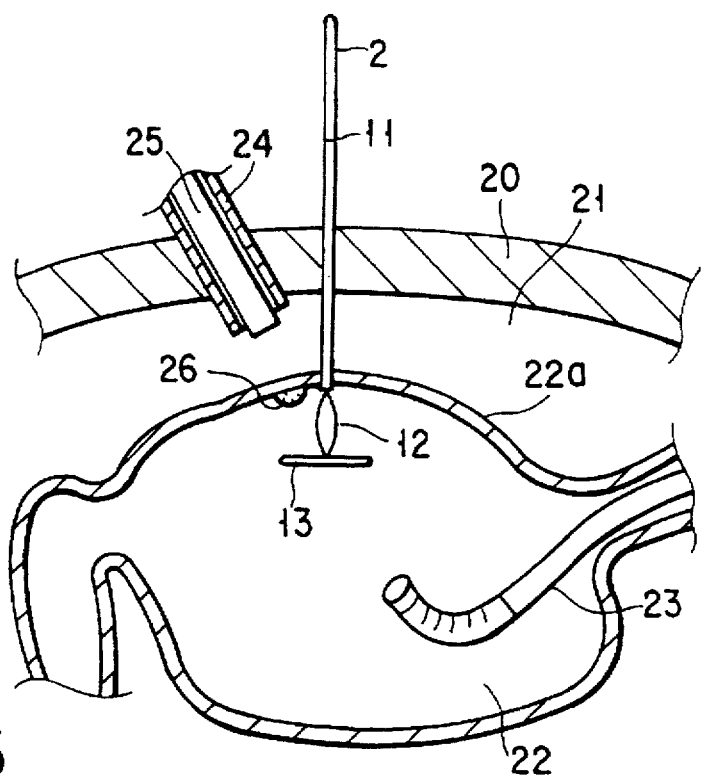
FIG. 3 shows a rod of the pulling member stuck into the stomach and rotated in it.

FIGS. 1A through 4 show a first embodiment of the present invention. A hang-up tool according to this embodiment which serves as the tool for manipulating an organ in human body comprises a centesis or penetration needle 1 shown in FIG. 1A, a pulling member (or means) 2 shown in FIG. 1B and a sheath (or manipulator means) 3 shown in FIG. 1C.

The penetration needle 1 includes an elongated pipe-like needle body 5 made of stainless steel, for example, and having a hollow portion 4 therein. A front tip 6 so sharp as to penetrate the somatic layer of a human body and organs in the human body is formed at the front end of the needle body 5. The front tip 6 may be made of a material different from that of the needle body 5 and fixed to the front end of the needle body 5.

The outer circumference of the needle body 5 except that of the front tip 6 is coated with an insulating member 7, which is a heat-shrinkable tubing attached to or an insulating film coated on the outer circumference of the needle body 5.

The insulating member 7 which is an insulating tubing or pipe may be bonded to the outer circumference of the needle body 5. This insulating tubing serving as the insulating member 7 is made of teflon, silicon, polyurethane, or polyethylene.

Hand side ends of the needle body 5 and the insulating member 7 are connected and fixed to a hand side body 8. A power source cord connecting pin 9 is projected from a side of the hand side body 8 and its basic end is connected to the needle body 5. High frequency current can thus flow from it to the front tip 6 through the needle body 5. A rubber cap 10 which serves as an insulator is detachably attached to the basic end of the hand side body 8.

The pulling member 2 includes a manipulating rod 11 inserted into its hollow portion 4 and made of insulating material. A wire (or line member) 12 extends from the front end of the manipulating rod 11, passing through a through-hole 14 in the center of a slender rod-like stopper rod 13, so that the stopper rod 13 can be bound to the front end of the manipulating rod 11 through the wire 12.

The wire 12 may be a stainless steel line, or a silk, nylon, polypropylene or bioabsorbing thread such as the suture. The manipulating rod 11 and the wire 12 may be connected to each other by a detachable joint. The stopper rod 13 may be made of bioabsorbing material. It can be inserted into the hollow portion 4 of the penetration needle 1 when its manipulating rod 11 and rod 13 are made like a straight line. More specifically, the rod 13 is kept at a first position at which it is aligned, like a straight line, with the manipulating rod 11 in the axial direction thereof, when the pulling member 2 is to be stuck into the human body, and it can be swung to a second position substantially perpendicular to the first position when the pulling member 2 is stuck into the human body.

The sheath 3 is a hard pipe. At least the rod 11 of the pulling member 2 can be inserted into a hollow portion 15a of this hard pipe 15. Further, air-tightness can be kept between the rubber cap 10 and the manipulating rod 11 when the pulling member 2 is inserted into the hollow portion 4 of the penetration needle 1.

The sheath 3 and the rod 11 of the pulling member 2 can be fixed to each other when the operator holds the hand side end of the sheath 3 and the rod 11 of the pulling member 2 at the same time, while keeping the rod 11 of the pulling member 2 inserted into the hollow portion 15a of the sheath 3.

It will be described how the above-described hang-up tool is operated. The hang-up tool is used in a surgical operation of cutting off an affected part 26 such as cancerous cells caused in a wall 22a of the stomach 22 of a patient as shown in FIG. 2, while an operator is observing the part 26 through an endoscope. FIG. 2 shows the penetration needle 1 stuck into a belly wall 20 and the wall 22a of the stomach 22. An endoscope 23 is previously inserted into the stomach 22 of the patient before the penetration needle 1 is stuck into it.

When the surgical operation is to be conducted, the stomach 22 is swelled, while supplying air into it through the endoscope 23. A trocar 24 is inserted into the belly wall 20 and a laparoscope 25 is inserted into a body cavity 21 through the trocar 24. Light is shot this time to the stomach wall 22a through a window at the front of the endoscope 23. This light can pass through the stomach wall 22a. When that portion of the stomach 22 through which the light passes is checked through the laparoscope 25, therefore, the position of the affected part 26 such as cancerous cells caused in the stomach wall 22a can be confirmed.

After the position of the affected part 26 is confirmed, the penetration needle 1 of the first hang-up tool is stuck into the belly wall 20 and the stomach wall 22 of the patient, respectively, as shown in FIG. 2. The pulling member 2 is previously inserted this time into the needle body 5 of the penetration needle 1. In short, the manipulating rod 11 and the rod 13 of the pulling member 2 which have been kept like a straight line are inserted into the hollow portion 4 of the needle body 5. A high frequency power source cord 27 is then connected to the power source cord connecting pin 9 of the hand side body 8.

The penetration needle 1 is stuck into the belly wall 20 and then into that portion of the stomach wall 22a which is around the affected part 26 confirmed. High frequency current is supplied to power source cord connecting pin 9 through the high frequency power source cord 27 during this sticking work of the penetration needle 1. High frequency current is thus caused to flow from the power source cord connecting pin 9 to the front tip 6 through the needle body 5. Therefore, the penetration needle 1 can be more easily stuck into the belly and stomach walls 20 and 22a while applying high frequency cutting to them.

When the member 2 is pushed into the stomach 22, the rod 13 is swung round its through-hole 14 and kept stable in the stomach 22. The penetration needle 1 is then removed out of the belly wall 20. The pulling member 2 is thus left in a hole of the belly wall 20 opened by the penetration needle 1, as shown in FIG. 3. Pressure in the stomach 22 is reduced under this state through the endoscope 23.

The basic end portion of the manipulating rod 11 of the pulling member 2 which is projected outside the belly wall 20 is then inserted into the hollow portion 15a of the sheath 3. The sheath 3 is further inserted into the body cavity 21, using the manipulating rod 11 as its guide. The manipulating rod 11 of the pulling member 2 is two times or more longer than each of the penetration needle 1 and the sheath 3. When the sheath 3 is stuck into the body cavity 21, therefore, the manipulating rod 11 is projected outside from the hand side end of the sheath 3 before the front end of the hard pipe 15 is inserted into the body cavity 21. This prevents the manipulating rod 11 from being dropped into the body cavity 21.

Figure 4:
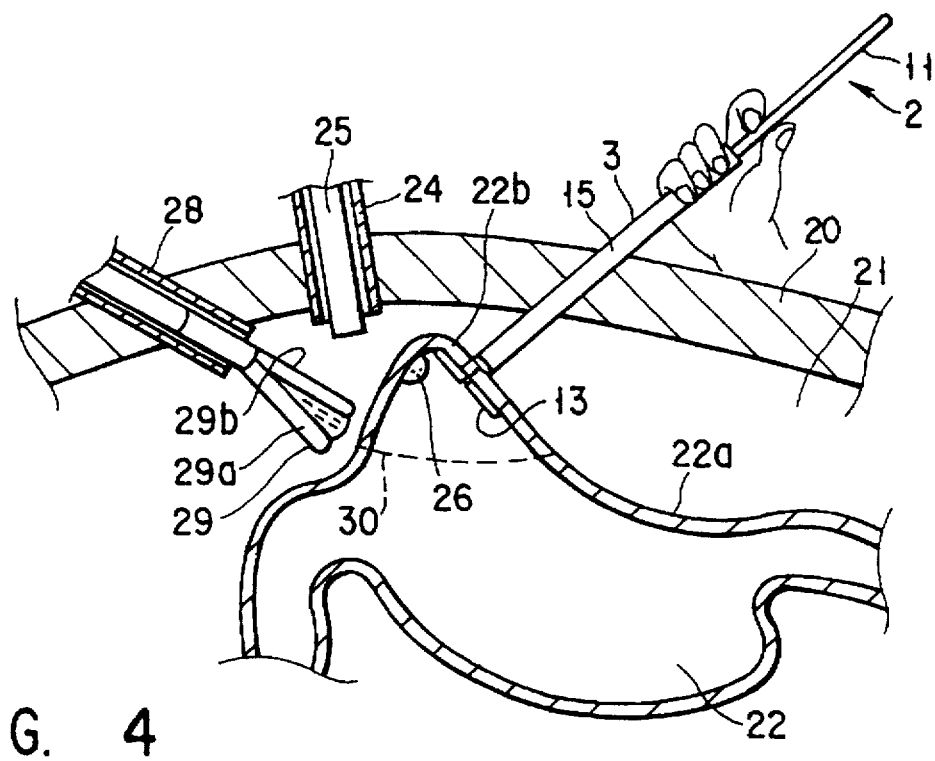
FIG. 4 shows the operator fixing a manipulator rod of the pulling member in the sheath.
Figure 5A:
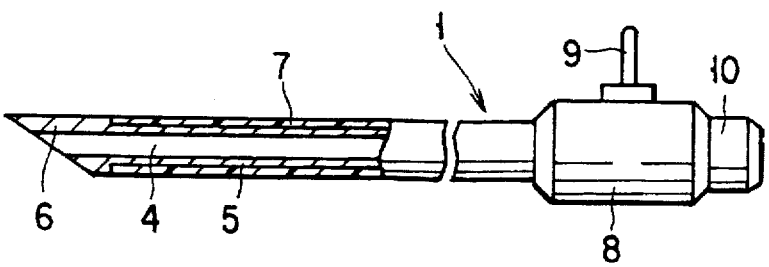
FIG. 5A is a side view showing a penetration needle of the hang-up tool according to a second embodiment of the present invention, said needle being partly sectioned.
Figure 5B:
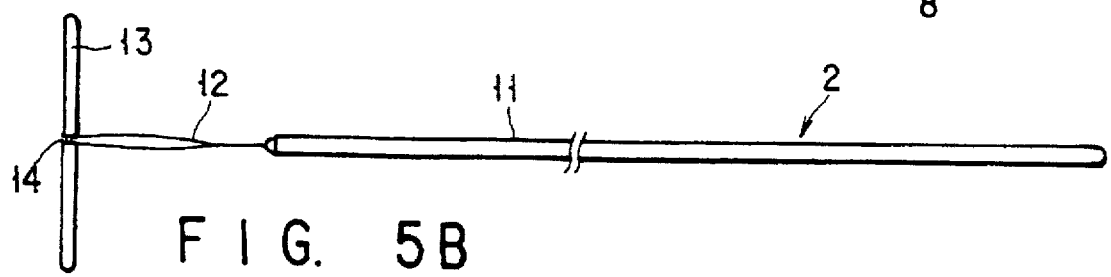
FIG. 5B is a side view showing a pulling member of the second hang-up tool.
Figure 5C:
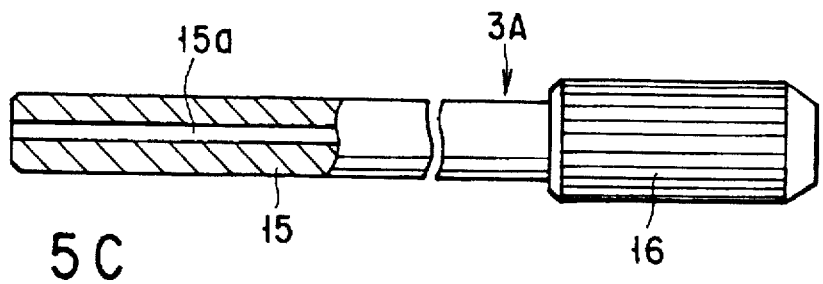
FIG. 5C is a side view showing a sheath of the second hang-up tool.

When the stomach wall 22a is sandwiched between the front end face of the hard pipe 15 and the rod 13 and the operator holds the hand side end portion of the sheath 3 and the pulling member 2 at the same time by his hand, as shown in FIG. 4, the sheath 3 and the manipulating rod 11 of the pulling member 2 can be fixed to each other.

The stomach 22 can be moved while operating the assembly of the pulling member 2 and the sheath 3 outside the belly wall 20. When the assembly is lifted and the manipulating rod 11 of the pulling member is tilted at a desired angle, as shown in FIG. 4, that portion of the stomach 22 which is around the affected part 26 can be lifted to such a position that allows it to be more easily cut off by a cutting member.

A linear cutter 29 is used as the cutting member in this case. It is provided with an anvil 29a and a cartridge 29b. It is inserted into the body cavity 21 through a trocar 28 at a position different from those of the trocar 24 and the hang-up tool.

After inserted into the body cavity 21, the linear cutter 29 is moved forward while keeping its axial direction aligned with a cut-off line of the stomach 22. That portion of the stomach 22 which is around the affected part 26 can be cut off by the linear cutter 29 cooperated with the hang-up tool.

After the stomach 22 is cut off in this manner, the linear cutter 29 is pulled outside the human body and a forceps (not shown) is inserted into the body cavity 21 of the patient through the trocar 28. The sheath 3 of the hang-up tool is then pulled out of the belly wall 20 while keeping a cut-off piece 22b of the stomach 22 clasped by the forceps.

The forceps, the cut-off piece 22b of the stomach 22 and the pulling member 2 are pulled out of the trocar 28. It is finally confirmed whether or not blood is shed from the cut-off line 30 of the stomach 22 left in the body cavity 21. Process such as high frequency coagulation and spraying of hemostatic and fibrin will be applied to the line 30, if necessary.

Air supplied into the stomach 22 may leak into the duodenum during the surgical operation. As the result, the duodenum and jejunum are swelled to thereby disturb the operation. In order to prevent this, a balloon may be previously set in the duodenum or the duodenum may be clamped from outside by the forceps.

In the case of this hang-up tool, the sticking of the penetration needle 1 into the belly and stomach walls 20 and 22a can cooperate with the high frequency cutting. Therefore, sticking force can be made less and the penetration needle 1 can be prevented from suddenly sticking out into the stomach 22. This can prevent blood vessels and organs from being unexpectedly damaged, thereby making the operation safer. Particularly the stomach wall 22a can be stuck out before its mucous membrane extends. When high frequency current is not used, however, the mucous membrane extends to such an extent that allows it to almost contact the mucous membrane on the rear wall of the stomach 22 before the penetration needle 1 is stuck into the stomach 22. When the penetration needle 1 is stuck into the stomach 22 at the instant the mucous membrane on the front wall of the stomach 22 extends to this extent, there is the possibility that it may be stuck into the rear wall of the stomach 22 and sometimes into organs and blood vessels behind the rear stomach wall. These organs and blood vessels may be unexpectedly damaged in this case. According to the hang-up tool of the present invention, however, this possibility can be avoided with a higher reliability and the penetration needle 1 can be stuck into the stomach 22 with a higher safety.

Further, the hard pipe 15 of the sheath 3 has a sufficient strength. In FIG. 4, therefore, the lifting direction of the stomach 22 can be freely and three-dimensionally changed. This makes it possible to cut off the affected part 26 as less as possible. After the surgical operation, therefore, the stomach 22 left can keep its function as it was.

Particularly when the volume of the affected part cut off is large in the vicinity of the pylorus and cardia of the stomach, stenosis may be caused. The sheath 3 of the present invention, however, can make this possibility less. When the affected part 26 of the stomach 22 is to be lifted, it is sometimes disturbed by adhesion between the stomach 22 and its surrounding tissues, depending upon what position of the stomach 22 the affected part 26 occupies. The adhesion must be excised in this case by the forceps inserted into the body cavity 21 and by the supersonic suction unit. When the sheath 3 of the present invention is three-dimensionally operated this time, however, appropriate counter-traction can be applied to the adhesion to thereby make it easier to excise the adhesion.

Although the affected part 26 of the stomach 22 has been cut off in the above-described example, the present invention can also be applied to lacunar organs such as large and small intestines and other organs such as lung, womb and bladder.

FIGS. 5A through 7 show a second embodiment of the present invention. The sheath (or manipulating means) 3 of the first embodiment is changed as shown in FIG. 5C. In short, a sheath 3A includes the hard pipe 15 and a fixing member 16 freely rotatably attached to the base end of the hard pipe 15. The pulling member 2 can be inserted into the hollow portion 15a of the hard pipe 15.

A mechanism for changing the inner diameter of the hollow portion 15a of the hard pipe 15 as the fixing member 16 is rotated is arranged in the fixing member 16. When the pulling member 2 is inserted into the hollow portion 15a of the hard pipe 15 and the fixing member 16 is rotated to make the inner diameter of the hollow portion 15a smaller, the pulling member 2 inserted can be fixed at a desired position.

It will be described how the above-described second hang-up tool is operated. The penetration needle 1, in the needle body 5 of which the pulling member 2 is inserted, is stuck into the belly and stomach walls 20 and 22a and then pulled out of the belly wall 20, leaving the pulling member 2 there. The sheath 3A is inserted into the body cavity 21, using the manipulating rod 11 as its guide.

Figure 6:
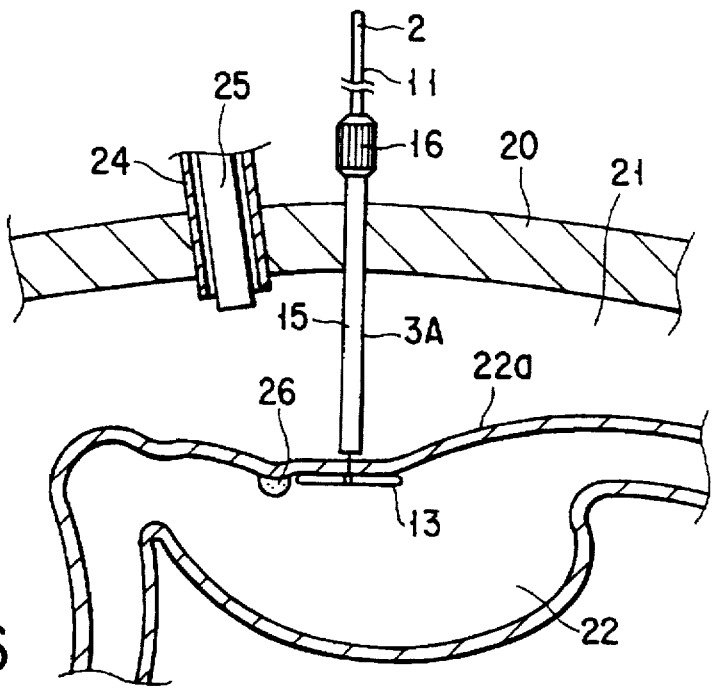
FIG. 6 shows the stomach wall sandwiched between a rod and the .sheath of the pulling member of the second hang-up tool.
Figure 7:
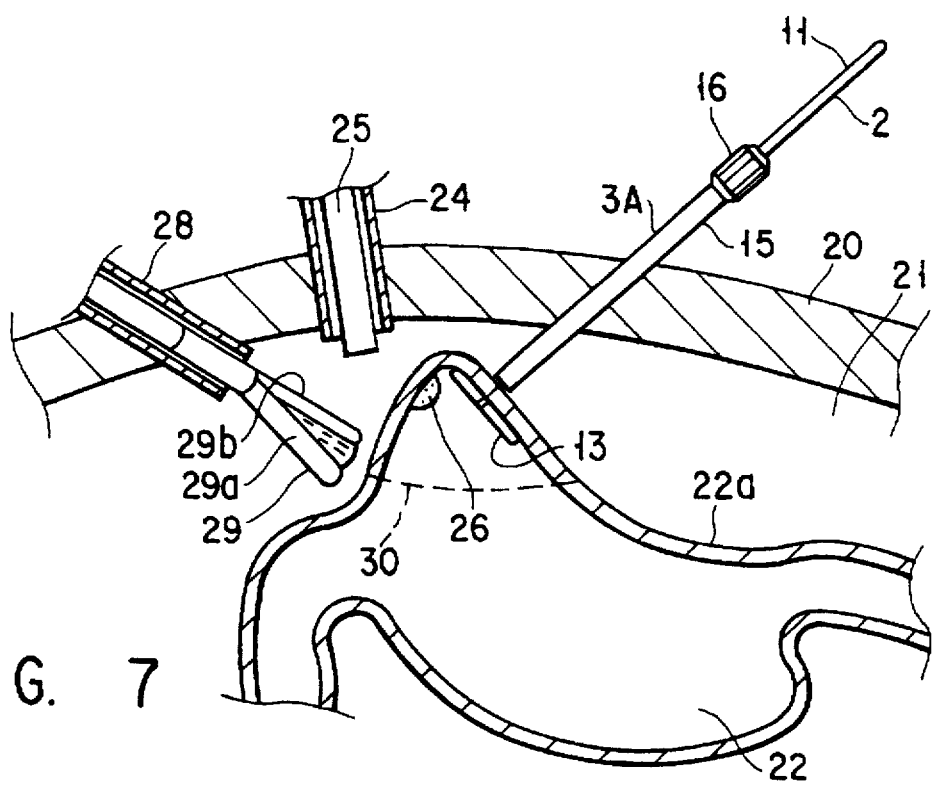
FIG. 7 is a view intended to explain how an intended part of the stomach wall is cut off by using the second hang-up tool.

The stomach wall 22a is sandwiched between the front end face of the hard pipe 15 and the rod 13, as shown in FIG. 6, and the fixing member 16 is rotated under this state. The inner diameter of the hollow portion 15a of the hard pipe 15 is made smaller by the fixing member 16 thus rotated, so that the manipulating rod 11 of the pulling member 2 and the hard pipe 15 can be fixed to each other. When the operator manipulates the assembly of the pulling member 2 and the sheath 3A outside the belly wall 20, therefore, the stomach 22 can be freely changed in shape.

Following same steps as those of the first embodiment, the affected part 26 of the stomach 22 is cut off. After this cutting-off, the cut-off piece 22b of the stomach 22 is clamped by the forceps (not shown) inserted through the trocar 28. The fixing member 16 is rotated backward to make the manipulating rod 11 free and the sheath 3A is then pulled out of the belly wall 20. Thereafter, same steps as those of the first embodiment will be taken.

Figure 8:
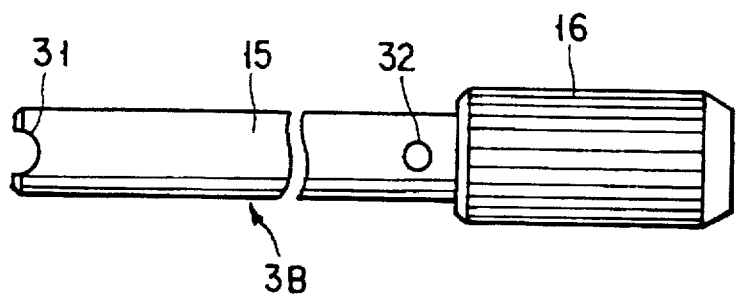
FIG. 8 is a side view showing a sheath of the hang-up tool according to a third embodiment of the present invention.
Figure 9:
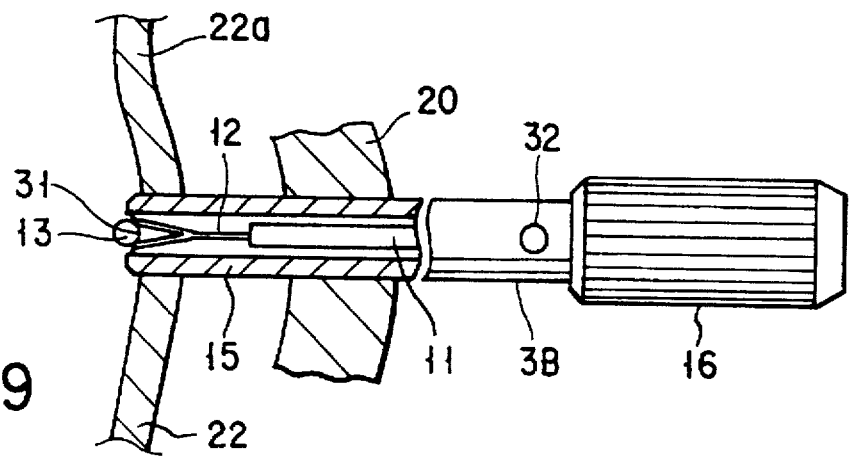
FIG. 9 is a view intended to explain how the sheath of the third hang-up tool is operated.

FIGS. 8 and 9 show a third embodiment of the present invention. The sheath 3A (see FIG. 5C) of the second embodiment is further changed in this example. Same components as those of the second embodiment shown in FIG. 5C will be denoted by same numeral references in FIGS. 8 and 9, and they will be described only when needed. As shown in FIG. 8, a semi-circular cut-away portion 31 is provided at the front end of the hard pipe 15 of a sheath 3B. Further, a marker 32 is arranged in the outer circumference of the hard pipe 15 at the hand side portion thereof. It is at such a position that corresponds to an arc face of the cutaway portion 31.

According to this third embodiment, the cut-away portion 31 and the rod 13 can be more accurately position-fixed because the manipulating rod 11 can be inserted into the cut-away portion 31 of the hard pipe 15, as shown in FIG.

9, when the manipulating rod 11 and the sheath 3B are fixed to each other by the fixing member 16. The direction of the rod 13 can also be more accurately confirmed by viewing the marker 32 outside the belly wall 20.

Further, the longitudinal axis of the rod 13 of the pulling member 2 and the axial direction of the linear cutter 29 can be more easily positioned when the marker 32 of the hard pipe 15 is faced the direction of the trocar 28 in which the linear cutter 29 is inserted. When the assembly of the pulling member 2 and the sheath 3B is operated outside the belly wall 20 and it cooperates with the linear cutter 29, while changing the shape of the stomach 22, therefore, the operation of cutting off the affected part 26 of the stomach 22 can be achieved at a higher speed and with a higher reliability.

Figure 10:
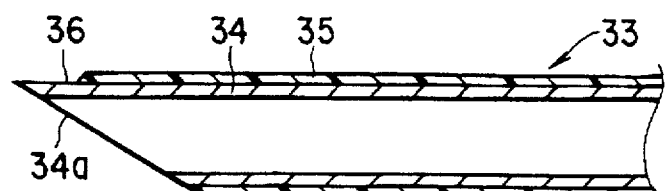
FIG. 10 is a vertically-sectioned view showing a penetration needle of the hang-up tool according to a fourth embodiment of the present invention.

FIG. 10 shows a fourth embodiment of the present invention. The penetration needle 1 of the first embodiment is changed as follows in this case. The front end of a needle body 34 of a penetration needle 33 is obliquely cut away to form a sharp cut-away portion 34a and the whole outer circumference of the needle body 34 of the penetration needle 33 except the sharp front of the cut-away portion 34a is coated with an insulating member 35.

Further, the sharp front of the cut-away portion 34a of the needle body 34 forms a front tip 36 which is not coated with the insulating material 35. The front tip 36 of the needle body 34 is thus made smaller in outer diameter than the penetration needle 33, although the front tip 6 in the first embodiment is same in outer diameter as the penetration needle 1.

Figure 11:
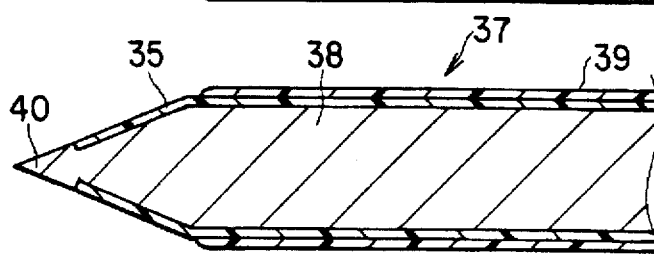
FIG. 11 is a vertically-sectioned view showing a penetration needle of the hang-up tool according to a fifth embodiment of the present invention.

FIG. 11 shows a fifth embodiment of the present invention. A penetration needle 37 comprises an inner needle 38 and an outer cylinder 39 in which the inner needle 38 is inserted. The outer cylinder 39 is made of insulating material. The outer circumference of the inner needle 38 except a front tip 40 is coated with the insulating material 35.

According to the above-described fourth through fifth embodiments, those holes in the stomach wall which are opened by the front tips 36 and 40 can be made smaller than the outer diameter of each of the penetration needles 33 and 37. When the sheath 3B is inserted into the holes after the penetration needles 33 and 37 are pulled out of the belly wall 20, therefore, living tissues more closely adhere to the outer circumference of the sheath 3B, thereby preventing air in the stomach from being leaked.

Further, the outer diameter of the hard pipe 15 which forms the sheath 3B can be made smaller. That area of living tissues of the patient which may be damaged by the hard pipe 15 can be made smaller, accordingly.

Figure 12:
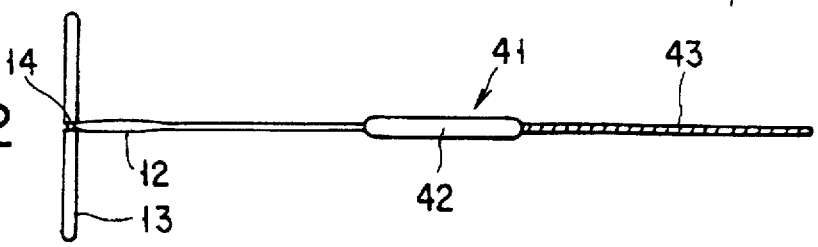
FIG. 12 is a side view showing a pulling member of the hang-up tool according to a sixth embodiment of the present invention.

FIG. 12 shows a sixth embodiment of the present invention. In the case of a pulling member 41, its manipulating rod 42 is made shorter than that in the pulling member 2 of the first embodiment, and a manipulating wire 43 is connected to the hand side end of the manipulating rod 42.

Figure 13:
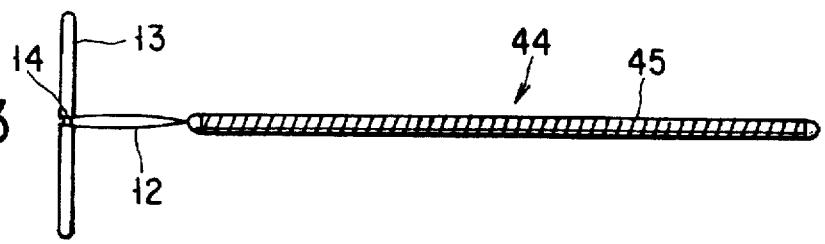
FIG. 13 is a side view showing a pulling member of the hang-up tool according to a seventh embodiment of the present invention.

FIG. 13 shows a seventh embodiment of the present invention. A pulling member 44 in this example includes no manipulating rod 42 but it is instead formed only by a manipulating wire 45.

According to the above-described sixth and seventh embodiments, the cut-off piece of the stomach can be more easily pulled out of the human body after this cutting-off is finished because the manipulating wires 43 and 45 are more flexible.

Figure 14:
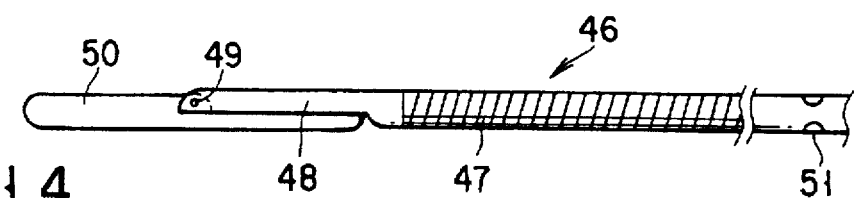
FIG. 14 is a side view showing a pulling member of the hang-up tool according to an eighth embodiment of the present invention.
Figure 15:
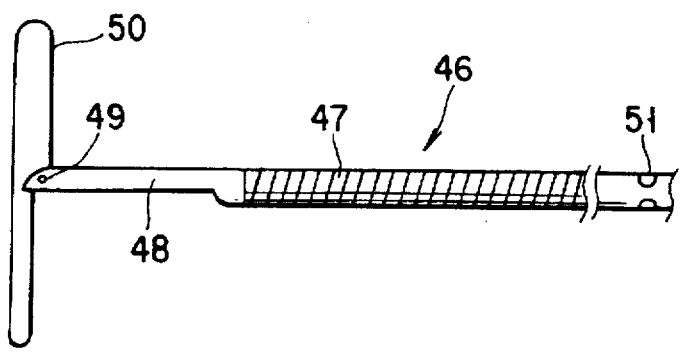
FIG. 15 is a side view showing the pulling member of the eighth hang-up tool.

FIGS. 14 and 15 show an eighth embodiment of the present invention. A pulling member 46 in this example comprises a flexible coil 47 and a front member 48 extending from the front end of the flexible coil 47.

Further, a rod 50 is freely swingably connected to the front member 48 by a hinge pin 49. In addition, markers 51 which show the direction of the rod 50 are provided on the hand side portion of the flexible coil 47.

According to the above-described eighth embodiment, the direction of the rod 50 can be confirmed without assembling the rod 50 with the sheath 3.

Since the rod 50 is rotatable, it can be moved into substantially axial alignment with the flexible coil 47 after the removed part of the stomach wall is held by a pair of forceps. Once the rod 50 has been aligned with the coil 47, the pulling member 46 can be releases from the removed part of the stomach wall. This facilitates the recovery of the removed part of the stomach wall.

FIGS. 16A through 21 show a ninth embodiment of the present invention. The ninth hang-up tool comprises a penetration needle 61 shown in FIG. 16A, a pulling member (or traction means) 62 shown in FIG. 16B and a sheath (or manipulating means) 63 shown in FIG. 16C.

The penetration needle 61 includes an elongated pipe-like needle body 65 having a hollow portion 64 therein. The needle body 65 has an outer diameter $\phi$ of about 2.8 mm. It has a front tip 66 so sharp as to be stuck into body walls and organs in the human body.

The outer circumference of the needle body 65 is covered by an insulating member 67 which is a transparent heat-shrinkable tube. Hand side ends of the needle body 65 and the insulating member 67 are bonded and fixed to a hand side body 68.

Figure 17:
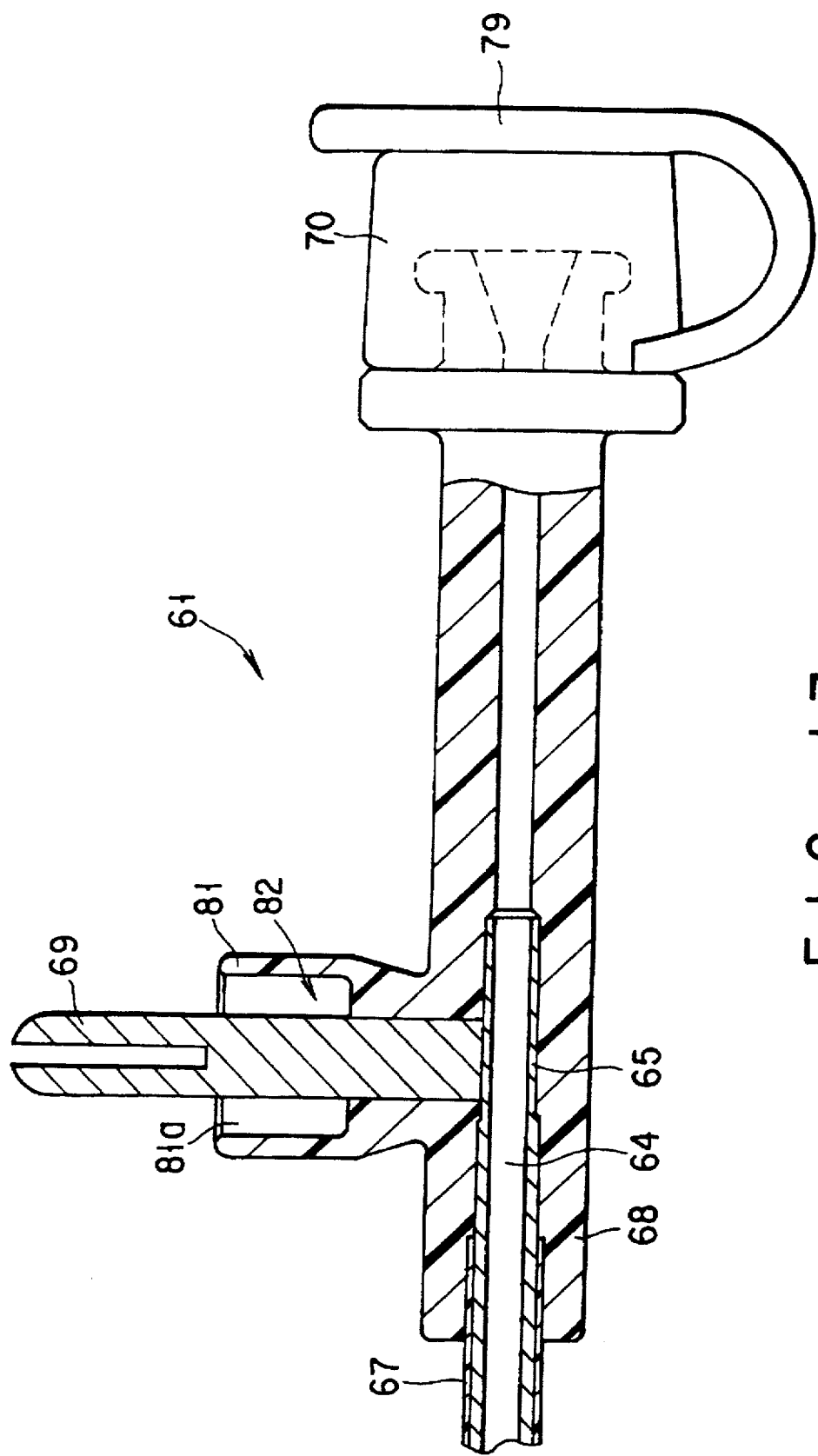
FIG. 17 is a side view showing the hand side portion of the needle of the ninth hang-up tool, said portion being partly sectioned.

The hand side body 68 is made of plastics such as polycarbonate and polystyrene which are high in transparence. A power source cord connecting pin 69 is projected from a side of the hand side body 68, as shown in FIG. 17. Its inner end is connected to the needle body 65 only by adhesive. High frequency current can be caused to flow from it to the front tip 66 through the needle body 65.

Further, a projection 81 is projected from the side of the hand side body 68, enclosing the power source cord connecting pin 69. Formed in its outer end portion is a recess 81a. The outer end portion of the power source cord connecting pin 69 is projected from the recess 81a along the axial center thereof. A clearance 82 is formed in this case between the pin 69 and the inner wall of the recess 81a. When the connector of a power source cord is to be connected to the pin 69, it is fitted into the clearance 82. The recess 81a of the projection 81 is set in its dimension not to stay water in it even when the power source cord is connected to the pin 69.

A rubber cap 70 is detachably attached to the base end of the hand side body 68. It has a lid 79. When this lid 79 is capped to the cap 70, air-tightness can be kept in the hand side portion of the penetration needle 61. The penetration needle 61 has a length of about 250 mm.

Figure 16A:
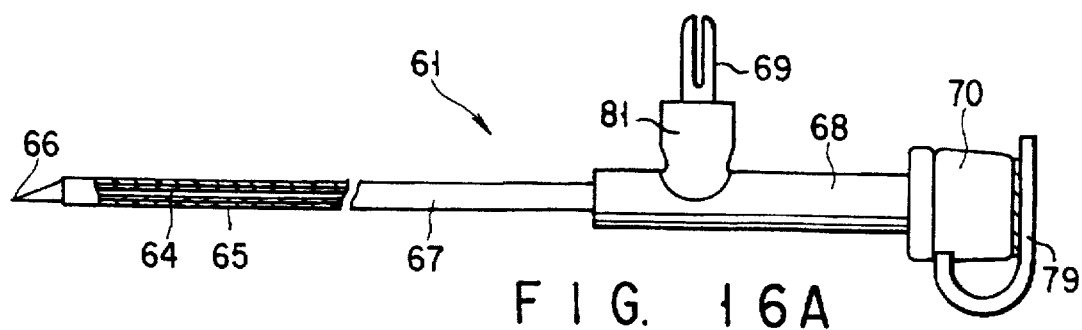
FIG. 16A is a side view showing a penetration needle of the hang-up tool according to a ninth embodiment of the present invention, said needle being partly sectioned.
Figure 16B:
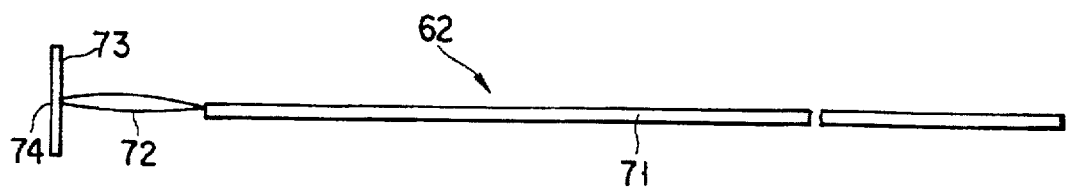
FIG. 16B is a side view showing a pulling member of the ninth hang-up tool.
Figure 16C:
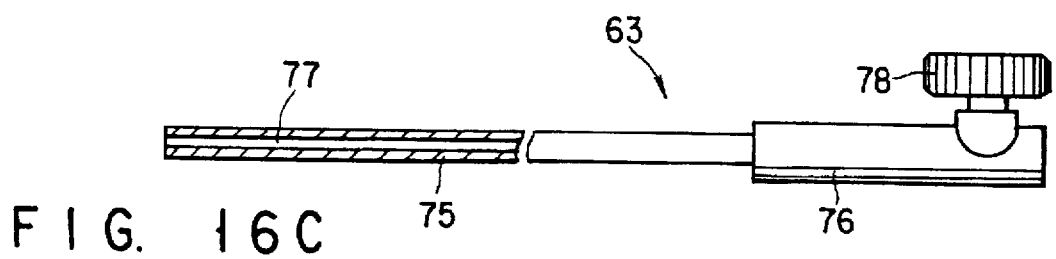
FIG. 16C is a side view showing a sheath of the ninth hang-up tool partly sectioned.
Figure 18:
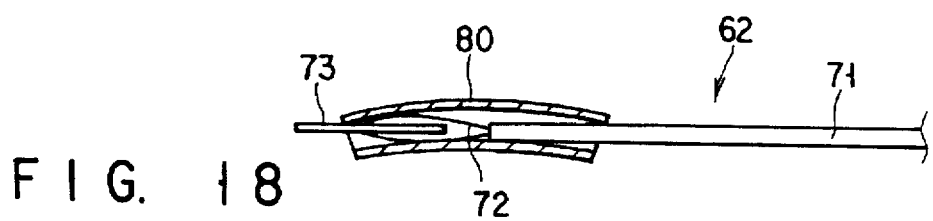
FIG. 18 is a side view showing a guide tube fitted onto the pulling member of the ninth hang-up tool.

The pulling member 62 includes a manipulating rod 71 which can be inserted into the hollow portion 64 of the penetration needle 61. A stopper rod (or stopper member) 73 is attached to the front end of the manipulating rod 71 through a wire (or line member) 72, as shown in FIG. 16B. The rod 73 is a slender rod-like member and a through-hole 74 is formed in the center of the rod 73, when viewed in the longitudinal direction of the rod 73. The wire 72 is passed through the through-hole 74.

The rod 73 is a slender hard rod-like member having a diameter $\phi$ of about 1 mm and a length of about 10–50 mm. Non-conductive material such as silk suture, No. 1-0 or 1 thick, regulated by the U.S. pharmacopoeia is used as the wire 72.

Before it is used, the pulling member 62 is covered from the front end portion of its manipulating rod 71 to the rod 73 by a guide tube 80 so as to keep the manipulating rod 71 and the rod 73 straight like a line. The guide tube 80 tends to curve at a curvature. Therefore, it does not come out of the pulling member 62. However, it can be easily detached from the pulling member 62 when the member 62 is to be used.

The manipulating rod 71 of the pulling member 62 is made at least 80 mm longer than each of the penetration needle 61 and the sheath 63. In this example, for example, the manipulating rod 71 has a length of about 450 mm and a diameter φ of about 1.5 mm. The guide tube 80 has an outer diameter larger than the inner diameter of the rubber cap 70. Therefore, it cannot be passed through the rubber cap 70 when the pulling member 62 is inserted into the penetration needle 61 while keeping the rubber cap 70 not capped by the lid 79.

Figure 19:
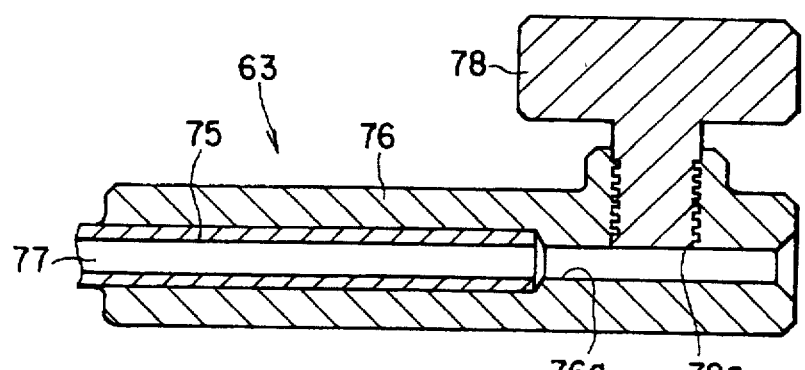
FIG. 19 is a vertically-sectioned view showing the hand side portion of the sheath of the ninth hang-up tool.

The sheath 63 includes a hard pipe 75 and a hand side body 76 connected to the hand side end of the hard pipe 75. A hole 76a through which the pulling member 62 can be passed is formed in the hand side body 76, as shown in FIG. 19. The hand side base end portion of the hard pipe 75 is bonded and fixed into the front end portion of the hole 76a of the hand side body 76.

The inner diameter of a hollow portion 77 in the sheath 63 is made so large as to allow the manipulating rod 71 of the pulling member 62 to pass through the hollow portion 77. The hard pipe 75 has an outer diameter φ of about 3.5 mm, which is a little larger than the outer diameter of the inserted portion of the penetration needle 61.

A fixing screw member 78 is screwed into a side of the hand side body 76. Its front threaded portion 78a can enter into the hollow portion 77 of the hand side body 76. When the manipulating rod 71 of the pulling member 62 is inserted into the hollow portion 77 of the hand side body 76 and the fixing screw member 78 is screwed into the hand side body 76, the manipulating rod 71 is pressed by the front end 78a of the fixing screw member 78 to friction-fix the pulling member 62 against the sheath 63. The sheath 63 has a length of about 250 mm.

Figure 20:
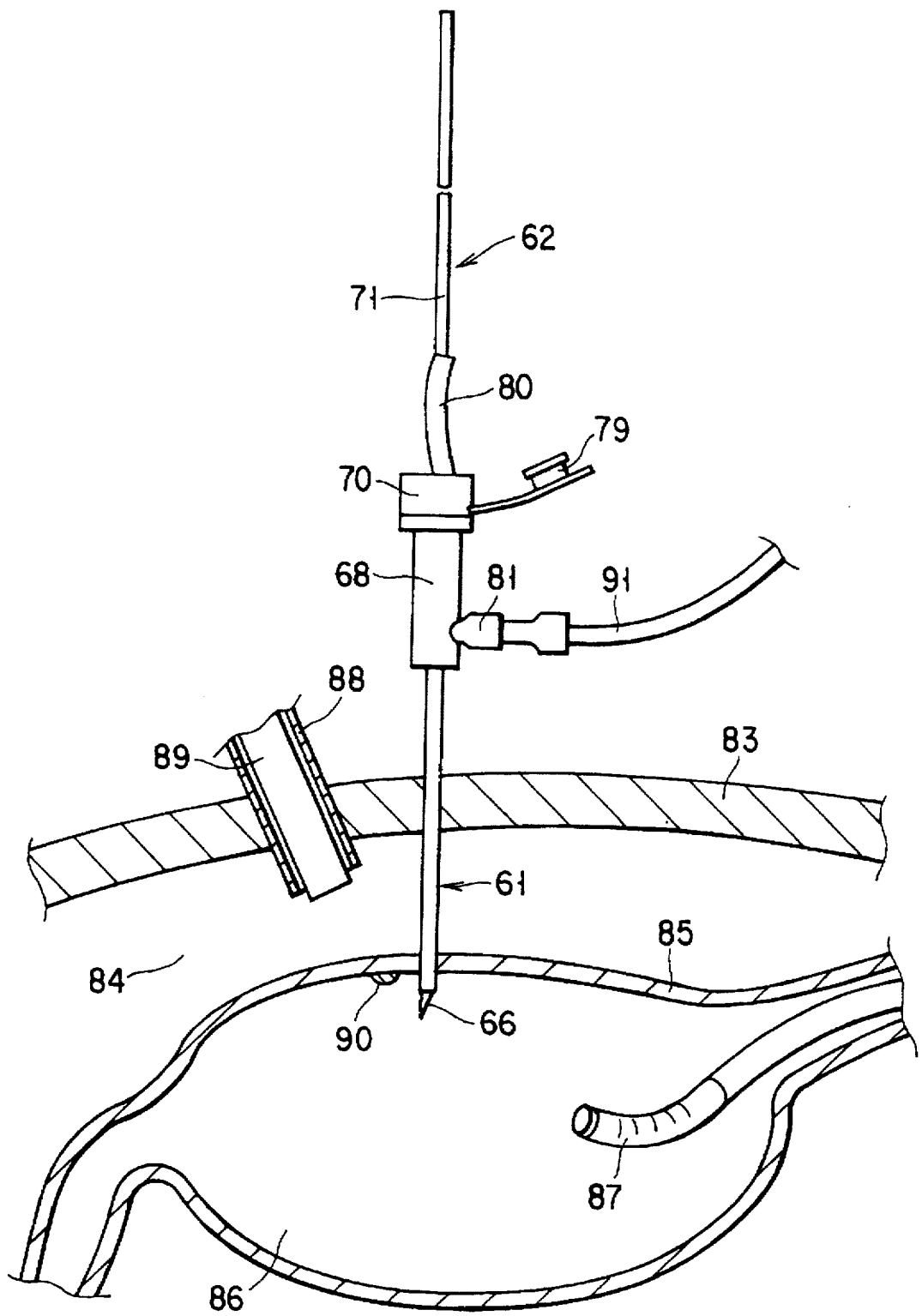
FIG. 20 shows a front tip of the penetration needle of the ninth hang-up tool stuck into the stomach wall.
Figure 21:
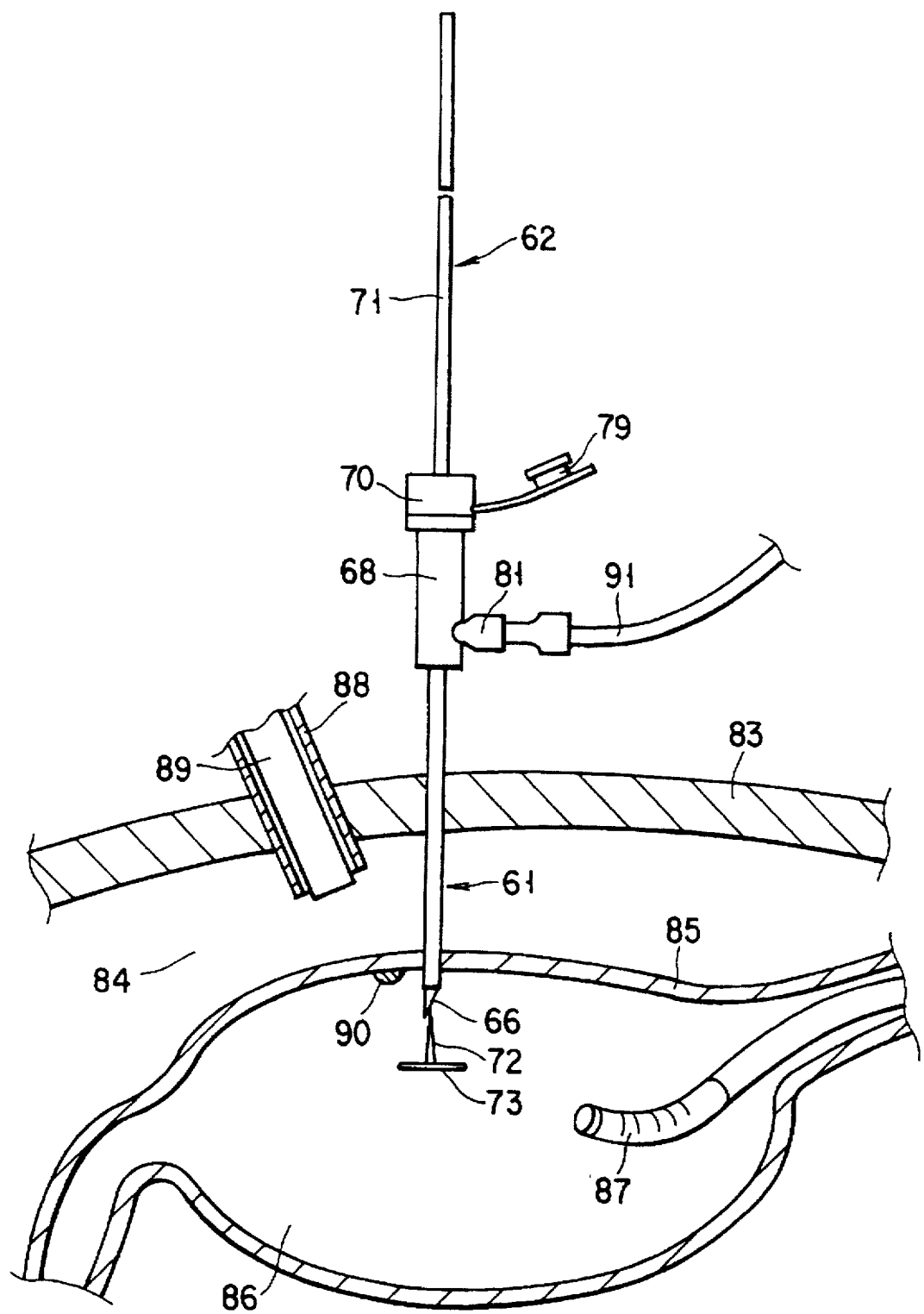
FIG. 21 is a view intended to explain how the pulling member of the ninth hang-up tool is used.

It will be described how the ninth hang-up tool is operated when the surgical operation of cutting off an affected part 90 such as cancerous cells caused in a wall 85 of the stomach 86 of a patient is to be conducted, as shown in FIG. 20. FIG. 20 shows the penetration needle 61 stuck into belly and stomach walls 83 and 85 of the patient. An endoscope 87 is previously inserted into the stomach 86 before the penetration needle 61 is stuck into it. A trocar 88 is inserted into the body cavity 84 through the belly wall 83 and a laparoscope 89 is inserted into it through the trocar 88. The stomach 86 in the body cavity 84 can be viewed by the laparoscope 89.

The surgical operation is started sticking the penetration needle 61 into the belly wall 83 and then into that portion of the stomach wall 85 which is around the affected part 90, as seen in the case of the first embodiment. The pulling member 62 is not inserted this time into the penetration needle 61.

When the sticking of the penetration needle 61 is finished as described above, the lid 79 of the rubber cap 70 is opened and the pulling member 62 covered by the guide tube 80 is inserted into the penetration needle 61. However, the guide tube 80 cannot be inserted into the rubber cap 70. As the manipulating rod 71 is pushed into the penetration needle 61, therefore, the rod 73, wire 72 and manipulating rod 71 are inserted into the penetration needle 61 in this order, leaving the guide tube 80 outside the rubber cap 70. The pushing of the penetration needle 61 continues until the rod 73 is projected outside from the front end of the penetration needle 61. When the rod 73 is projected into the stomach 86, the guide tube 80 and the penetration needle 61 are removed.

The sheath 63 is fitted onto the manipulating rod 71 of the pulling member 62 to insert the hard pipe 75 into the body cavity 84. When the stomach wall 85 is at a position where it is sandwiched between the front end of the hard pipe 75 and the rod 73, the fixing screw member 78 screwed into the hand side body 76 is screwed to press the manipulating rod 71 against the sheath 63 to friction-fix both of them. The following is same as in the first embodiment and description about it will be omitted accordingly.

To recover the cut-off piece after the removal of a part of the stomach wall 85, the following measures should be taken in order not to scatter cancer cells or the like in the body cavity. First, a recovery bag is inserted into the body cavity 84 through a trocar (not shown). Next, the wire 72 of the pulling member 62 is pulled with a cutting forceps inserted into the body cavity 84 through another trocar (not shown), thereby making the removed part of the stomach wall fall into the recovery bag. Then the sheath 63 and the manipulating rod 71 are removed from the body cavity 84 through the abdominal wall 83. Further, the recovery bag is closed and pulled from the abdominal wall, together with the trocar.

According to the ninth embodiment, the following effects can be attained.

a) The power source cord connecting pin 69 and the needle body 65 in the hand side body 68 are connected to each other only by adhesive, thereby making the cost lower;

b) The hand side body 68 is made of transparent material. Therefore, the adhesion of the pin 69 relative to the needle body 65 can be confirmed by eyes;

c) The rod 73 is connected to the manipulating rod 71 by the wire 72 such as silk thread. After the stomach 86 is partly cut off, therefore, the silk wire 72 can be easily cut in the body cavity 84 by the cutting forceps. This makes it easier to withdraw the cut-off piece of the stomach 86. In addition, the operation can be made simpler and safety. Further, the silk wire 72 is non-conductive. Even when the high frequency unit is caused to contact the manipulating rod 71 during the surgical operation, therefore, current cannot flow to the rod 73. Safety can be thus guaranteed and the cut-off piece of the stomach can be kept beautiful;

d) The freely openable rubber cap 70 is attached to the hand side body 68 of the penetration needle 61. When the penetration needle 61 is stuck into the belly and stomach walls, therefore, gas in the body cavity 84 and the stomach 86 can be prevented from leaking outside. This enables the surgical operation to be conducted smoothly;

e) The curved guide tube 80 used is cheap and it enables the manipulating rod 71 and the rod 73 to be kept straight like a line. The hang-up tool can be thus easily operated;

f) The hand side body 76 of the sheath 63 is made of transparent material. During the assembling of the hang-up tool, therefore, the adhesion of the hard pipe 75 relative to the hand side body 76 can be confirmed by eyes. In addition, the contact of the manipulating rod 71 of the pulling member 62 with the fixing screw member 78 can also be confirmed by eyes during the surgical operation;

g) The manipulating rod 71 of the pulling member 62 is made of hard material. The pulling member 62 can be thus more easily inserted into the penetration needle 61 and it can be more easily fixed to the sheath 63. Further, the outer diameter of the inserted portion of the sheath 63 is made larger than that of the inserted portion of the penetration needle 61. This prevents gas in the body cavity 84 from being leaked outside. Furthermore, the front end of the sheath 63 cannot enter into the hole in the stomach wall 85 which is opened by the penetration needle 61. This enables the stomach wall 85 to be sandwiched between the rod 73 and the hard pipe 75. Therefore, there is no possibility that the front end of the sheath 63 enters into the stomach 86 and that it is contacted with the affected part 90 to scatter malignant tumor such as cancer in the body cavity 84. Safety can also be guaranteed accordingly; and h) Each of the penetration needle 61 and the sheath 63 has a length of about 250 mm. This enables them to reach the rear wall of the stomach 86.

Figure 22:
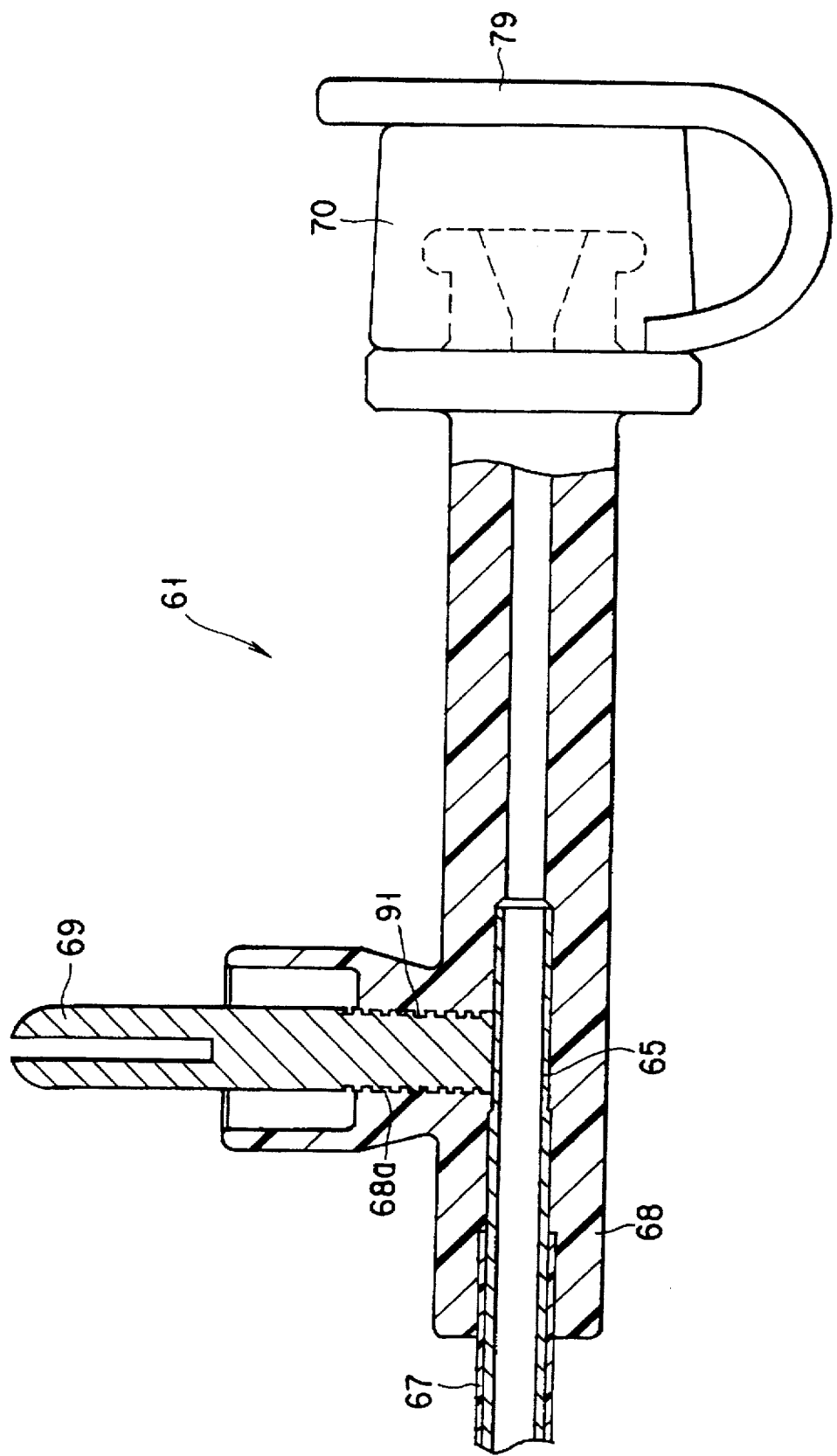
FIG. 22 is a side view showing a penetration needle of the hang-up tool according to a tenth embodiment of the present invention, said needle being partly sectioned at its hand side portion.

FIG. 22 shows a tenth embodiment of the present invention. This embodiment is a variation of the penetration needle 61 of the ninth embodiment (see FIG. 17). A hole 68a is formed in a side of the hand side body 68 of the penetration needle 61 in this example, extending in a direction perpendicular to the axial direction of the hand side body 68 and reaching the hollow portion 64 thereof. Further, a threaded portion 91 is formed in the base end portion of the power source cord connecting pin 69. The diameter of the hole 68a of the hand side body 68 is made substantially same as the root diameter of the threaded portion 91 of the pin 69.

The hand side body 68 is made of plastic material. When the power source cord connecting pin 69 is screwed into the hole 68a, therefore, the hole 68a is scraped off by the threaded portion 91 of the pin 69 to thereby form a self-tap thread in the inner face of the hole 68a. When the base end portion of the pin 69 is screwed until it strikes against the needle body 65, the pin 69 can be fixed to the hand side body 68.

The function of the tenth embodiment is same as that of the ninth and additional effects attained by the tenth embodiment are that the penetration needle 61 can be more easily and reliably assembled and that it can be provided at a lower cost.

Figure 23:
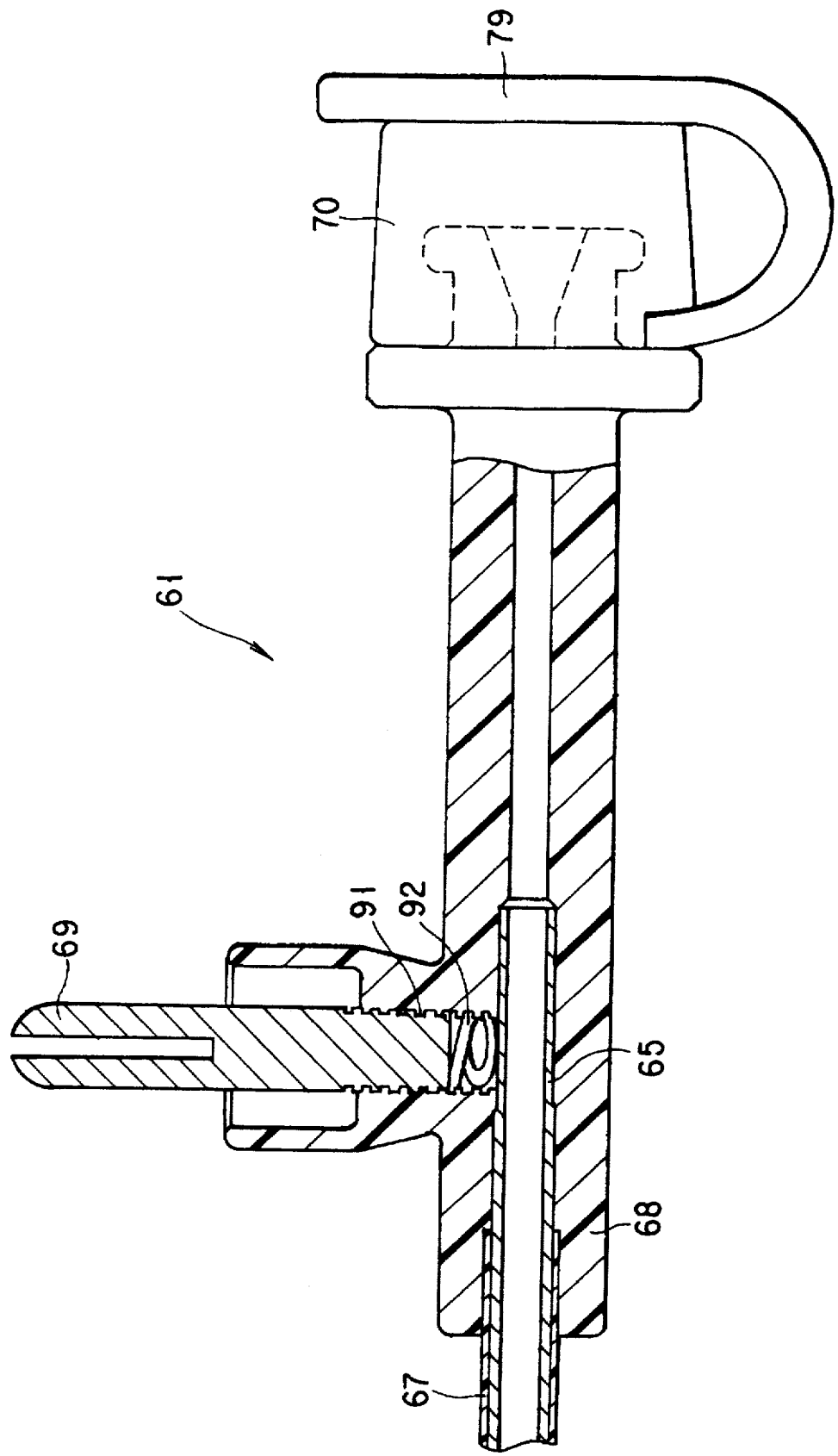
FIG. 23 is a side view showing a penetration needle of the hang-up tool according to an eleventh embodiment of the present invention, said needle being partly sectioned at its hand side portion.

FIG. 23 shows an eleventh embodiment of the present invention. This is a variation of the penetration needle 61 of the ninth embodiment (see FIG. 17). In this example, an elastic conductive member 92 which is a metal coil spring is arranged between the power source cord connecting pin 69 and the needle body 65. Other components and their arrangement are same as those of the ninth embodiment.

The conductive member 92 may be a metal plate spring, or it may be made of conductive material such as conductive silicon and aluminum foil. Any conductive material can be used as the member 92 if they are a little elastic or easily deformed.

The function of the eleventh embodiment is same as that of the ninth and additional effects attained by the eleventh embodiment are that electrical connection between the pin 69 and the needle body 65 can be made more reliable because of the conductive member 92 arranged between the pin 69 and the needle body 65, and that this electrical connection can be kept unchanged even as time goes by.

FIGS. 24 and 25 show a twelfth embodiment of the present invention. In this example, a solid guide rod 93 made of resin material such as fluorine and polyamide, or of insulating material such as ceramics, as shown in FIG. 24 is added to the ninth embodiment (see FIGS. 16A–21).

As shown in FIG. 25, the penetration needle 61 is stuck into the belly wall 83 and then into the body cavity 84. The guide rod 93 is then inserted from hand side into the hollow portion 64 of the penetration needle 61 under this state to project from the front end of the penetration needle 61.

A front end portion 94 of the guide rod 93 is struck against the stomach wall 85 to push it down. That position of the stomach wall 85 which is pushed down by the guide rod 93 is viewed this time through the endoscope 87 in the stomach 86, to thereby confirm the needle-stuck position of the stomach wall 85. The penetration needle 61 is then stuck into the stomach wall 85 along the guide rod 93.

The other function of this embodiment is same as that of the ninth and additional effects attained are that the sticking of the penetration needle 61 can be made easier because the sticking position of the needle 61 into the stomach 86 can be safely and reliably, confirmed by the guide rod 93, and that safety can be guaranteed when current is applied to the penetration needle 61 because the guide rod 93 is made of insulating material.

FIG. 26 shows a thirteenth embodiment of the present invention. This is a variation of the guide rod 93 of the twelfth embodiment (see FIGS. 24 and 25). In this example, a guide rod 95 comprises a hard rod (or line member) 96 made of metal such as stainless steel, a cover tube (or insulating member) 97 covering the hard rod 96, and adhesive 98 filled in both ends of the cover tube 97. The guide rod 95 is thus made as an insulator.

The function of the thirteenth embodiment is same as that of the twelfth and additional effects to those of the twelfth are that the guide rod 95 is so high in resistance to bending and curving that the sticking of the penetration needle can be more safely and reliably confirmed.

Figure 27:
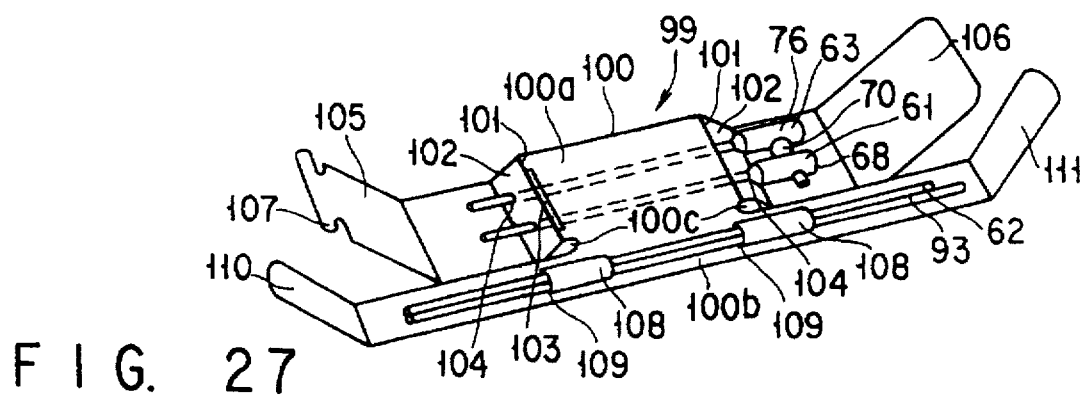
FIG. 27 is a perspective view showing a tray for the hang-up tool according to a fourteenth embodiment of the present invention, said tray being developed.
Figure 28:
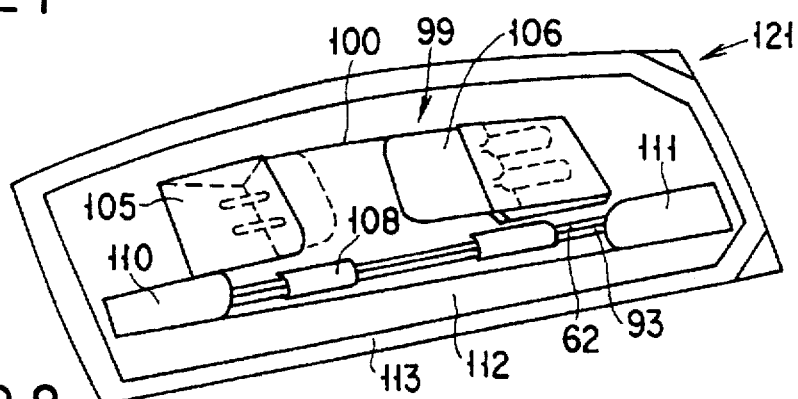
FIG. 28 is a perspective view showing the tray housed in a peel pack.

FIGS. 27 and 28 show a fourteenth embodiment of the present invention. In this example, the 5 penetration needle 61, pulling member 62, sheath 63, rubber cap 70 and guide rod 93 which are components of the twelfth embodiment are made a sanitized and disposable tool set, which is packed in a pack 121.

The pack 121 comprises a tray 99 shown in FIG. 27 and a peel pack 112 shown in FIG. 28. The tray 99 includes a tray body 100 for housing the above-mentioned components as shown in FIG. 27. It is made of resin such as polystyrene and polypropylene or by a thin plate of cardboard.

The tray body 100 comprises wide and narrow sections 100a and 100b. Slit-shaped cut-away portions 100c are formed between the wide section 100a and the narrow section 100b, extending inwards to some extent from both ends of these sections and leaving their connection area between these cut-away portions 100c, when viewed in the longitudinal direction of them.

The wide section 100a includes mount-forming bent portions 101 formed at both ends of the center connection area and in its horizontal direction. A slit 103 is formed in the top of one of the bent portions 101. Further, plural holes 104 are formed in slopes 102 of both bent portions 101 and each of them in one slope corresponds to its mate hole in the other slope.

First and second valley-forming bent-back portions 105 and 106 are formed at both ends of the wide section 100a when viewed in the longitudinal direction thereof. The first bent-back portion 105 includes a part 107 which is pushed into the slit 103.

Two arc members 108 are arranged on the narrow section 100b with an interval interposed between them in the longitudinal direction of the section 100b. Each of the arc members 108 is made hollow, thereby forming a hollow portion 109. Further, the narrow section 100b includes third and fourth valley-forming bent-back portions 110 and 111 formed at its both ends when viewed in its longitudinal direction.

The penetration needle 61 and the sheath 63 are inserted into holes 104 of the wide section 100a at their stuck portions so that their movement, up and down, right and left, can be limited. Their hand side bodies 68 and 76 have an outer diameter larger than that of each hole 104. Therefore, these hand side bodies 68 and 76 cannot be passed through the holes 104 in this case. The number of bent portions formed is not limited.

The push part 107 of the first bent-back portion 105 located on the front side of the penetration needle 61 and the sheath 63 is pushed into the slit 103, thereby protecting the front end of the penetration needle 61 and limiting the forward movement of the needle 61 and the sheath 63. When the second bent-back portion 106 is bent back, it covers and protects the hand side bodies 68 and 76 and limits the backward movement of the needle 61 and the sheath 63. The rubber cap 70 is placed between the hand side bodies 68 and 76.

The pulling member 62 and the guide rod 93 are inserted into the hollow portion 109 of each arc member 108 on the narrow section 100b, so that their movement, up and down, right and left, can be limited. When the third and fourth bent-back portions 110 and 111 are bent back, they limit the movement of the pulling member 62 and the guide rod 93 in the axial direction of the tray.

The peel pack 112 houses the tray 99, in which each of the components has been packed, as shown in FIG. 28. It is usually used as a pack sterilized by ethylene oxide gas. A heat seal area 113 is formed along the rim of the pack 112 to seal the pack.

Although the penetration needle 61, pulling member 62, sheath 63, rubber cap 70 and guide rod 93 which are the components of the twelfth embodiment have been packed in the peel pack 112, others may be packed in it in addition to them.

As described above, the components are inserted into holes 104 and 109 of the tray 99 and their movement, up and down, right and left, can be thus limited. Further, the rubber cap 70 is held between the hand side bodies 68 and 76 of the penetration needle 61 and the sheath 63 and first to fourth bent-back portions 105, 106, 110 and 111 are bent back to limit their movement in the axial direction of the tray 99. The tray 99 in which they have been packed, as described above, is further packed in the peel pack 10 112, which is then heat-sealed. By using the hang-up tool, the surgeon can open the peel pack 112, remove the tray 99 from the peel pack 112, open the second and fourth bent-back portions 106 and 111 of the tray 99, and pull components from the tray 66—without allowing germs to enter the peel pack 112 which has been sterilized.

According to the fourteenth embodiment, the following effects can be attained.

a) The tray 99 can be made by a thin cardboard plate. It is therefore cheap and it is suitable as a disposable product;

b) Components are inserted into holes 104 and 109 of the tray 99 and both ends of the tray 99 are bent on these components. Therefore, they can be more easily and reliably positioned and fixed in the tray and they cannot be broken and damaged during their transportation. In addition, the tip of the penetration needle 61 can be protected by the first bent-back portion 105;

c) The thickness of the tray 99 in which components are housed can be reduced to the maximum extent and the volume of the peel pack 112 can be thus made minimum. Therefore, the efficiency of sterilizing the packs can be made higher. In short, the volume of each pack is small and this enables a large number of packs to be sterilized at a time. The cost can be thus made lower; and d) Components needed are housed in the tray 99. When the hang-up tool is to be used, therefore, they can be carried from a place not sterilized to another place sterilized at a time. This is quite convenient for the user.

Figure 29:
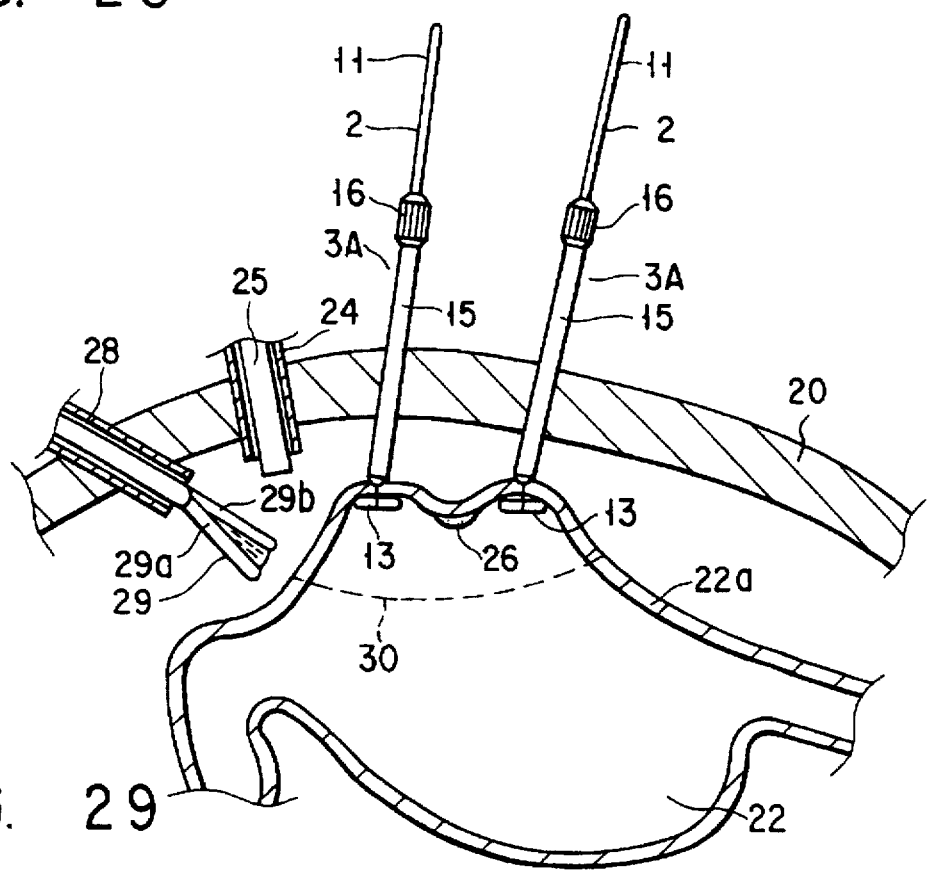
FIG. 29 is a view intended to explain how a pulling member of the hang-up tool according to a fifteenth embodiment of the present invention is used.

FIG. 29 shows a fifteenth embodiment of the present invention. In this example, plural or two second hang-up tools (see FIGS. 5A–7) are used. In the case of using the pulling member 2 as a single, the stomach wall is hung up as a point, in a case of using two pulling members 2, it is hung up as a line and in another case of using three or more pulling members 2, it is hung up as a plane. The number of the pulling members 2 used may be therefore changed, depending upon the size of affected part to be cut off.

According to the fifteenth embodiment, the stomach wall 22a of the patient can be hung up at a line connecting the two pulling members 2. The operation of moving the stomach wall 22a in any desired direction can be thus made easier.

Further, When a quite large area of the stock wall 22a must be hung up because the affected part of the stomach wall 22a is large, it can be solved by using plural pulling members.

Figure 30:
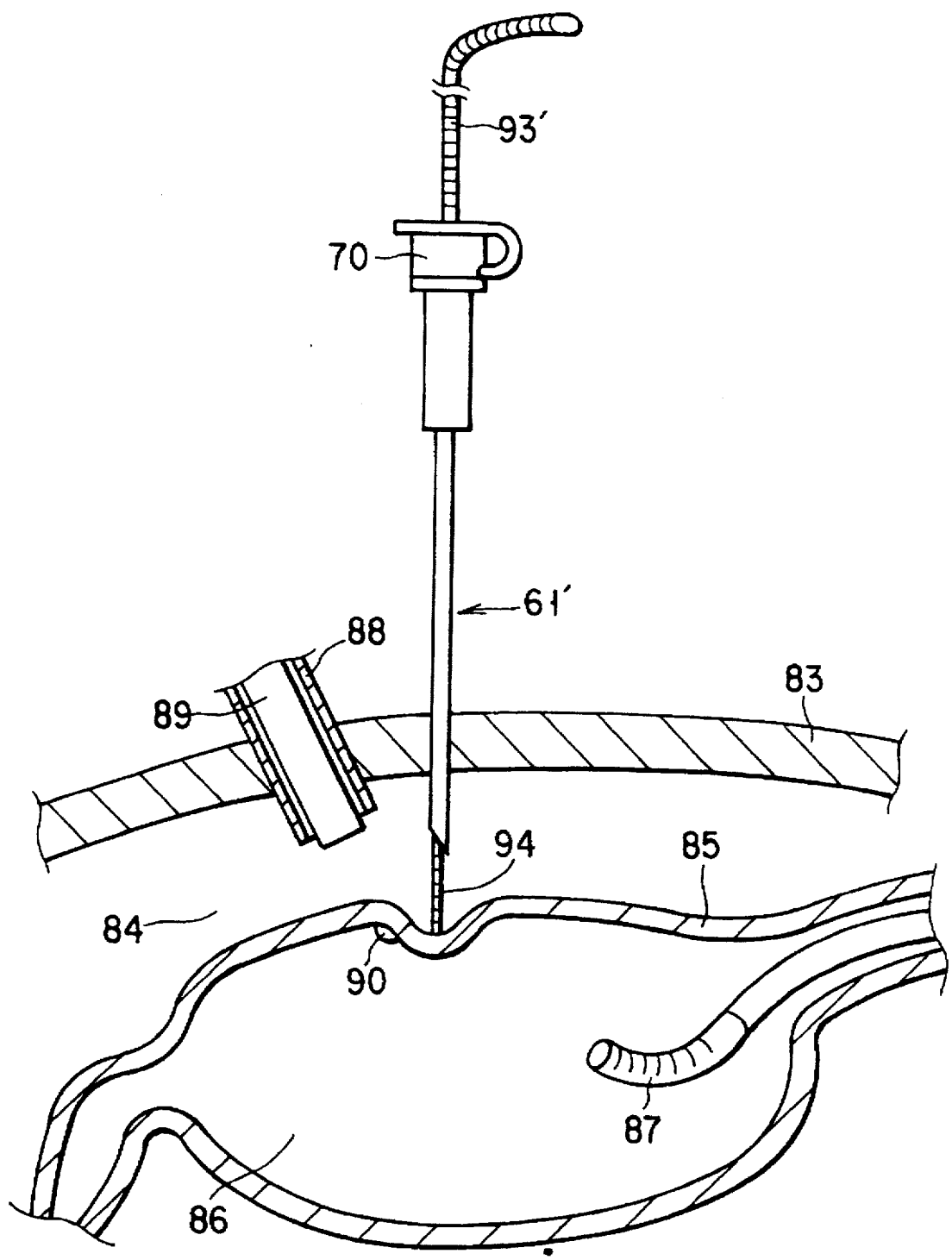
FIG. 30 is a view intended to explain how a guide rod of the hang-up tool according to a sixteenth embodiment of the present invention is used.

FIG. 30 shows a sixth embodiment of the present invention. In this example, the guide rod 93 of the twelfth embodiment (see FIGS. 24 and 25) is replaced by a guide member 93' made by a wire and the guide member 93' is combined with a penetration needle 61' which is not conductive and which is not covered by any insulating tube.

Other components used and effects attained are same as those of the twelfth embodiment.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A tool for manipulating tissue comprising:

a penetration needle having a hollow portion, said penetration needle being adapted to be stuck into a body cavity of a patient;

a pulling member insertable into the hollow portion of the penetration needle so as to be positioned in the body cavity of the patient, said pulling member comprising:

a rigid manipulating rod formed in a substantially straight line shape; and a stopper member pivotally connected to a front end of said manipulating rod, said stopper member being movable between positions that are aligned with or transverse to said straight line shape;

said pulling member being adapted to pull tissue in the body cavity; and a manipulator having a hollow portion through which the pulling member can be passed, said manipulator being adapted to be guided over said manipulating rod to be inserted into the body cavity of the patient after the penetration needle is removed therefrom, while said stopper member is left in the body cavity, wherein said manipulator is adapted to be positionally fixed relative to the pulling member and to be operable together with said pulling member to move the pulled tissue in a desired direction and to hold the pulled tissue at a desired position.

2. The tool according to claim 1, further comprising high frequency cauterizing means arranged at a front end of the penetration needle for high frequency cauterizing tissue stuck by the penetration needle, to thereby increase the penetration capability of the penetration needle.

3. The tool according to claim 2, wherein said penetration needle includes a conductive needle body and an insulating member covering the needle body except at a front end thereof, and said high frequency cauterizing means includes means for applying a high frequency current to the front end of the needle body which is not covered by the insulating member.

4. The tool according to claim 3, wherein said insulating member comprises a tube covering the needle body.

5. The tool according to claim 4, wherein said tube comprises one the group consisting of teflon, silicon, polyurethane and polyethylene.

6. The tool according to claim 3, wherein said insulating member comprises a film coated on the outer circumference of the needle body.

7. The tool according to claim 2, wherein said penetration needle includes a conductive needle body, an insulating member coated on at least an outer circumference of the conductive needle body, and a conductive front tip arranged at a front end of the needle body, and wherein said high frequency cauterizing means includes means for applying a high frequency current to the conductive front tip.

8. The tool according to claim 2, wherein said high frequency cauterizing means includes a power source cord connecting pin arranged on a portion of the penetration needle which is adapted to be maintained outside of the body cavity of the patient, said power source cord connecting pin being connectable to a high frequency power source.

9. The tool according to claim 1, wherein said stopper member is adapted to be held at a first position such that it is aligned with the manipulating rod in a straight line in an axial direction of the manipulating rod when the pulling member is inserted into the hollow portion of the penetration needle, and said stopper member is adapted to be swung to a second position substantially perpendicular to the first position when the manipulating rod is projected outside of a front end of the hollow portion of the penetration needle.

10. The tool according to claim 9, wherein said stopper member is made of a bioabsorbable material.

11. The tool according to claim 9, wherein said manipulating rod and said stopper member are coupled to each other by a line member.

12. The tool according to claim 11, wherein said line member comprises a wire.

13. The tool according to claim 11, wherein said line member comprises a thread.

14. The tool according to claim 1, wherein said manipulator means includes a hard pipe sheath and positioning means formed at a front end of the sheath for positioning a front end of said pulling member.

15. The tool according to claim 14, wherein said positioning means comprises a cut-away portion having one of a semicircular and arc shape, said cut-away portion being formed at the front end of said sheath.

16. The tool according to claim 15, wherein said sheath includes a marker representing direction of said cut-away portion.

17. The tool according to claim 1, wherein said manipulator includes:
a hard pipe sheath,
a connector connected to the sheath on an outer portion of said sheath which is adapted to be maintained outside of the body cavity of the patient, said connector having a hollow portion into which said pulling means is inserted,
a screw hole formed in a side of said connector, said screw hole having an inner end portion communicating with said hollow portion of said connector, and
a fixing member having an engaging end screwed into said screw hole and projected into the hollow portion of said connector to press and fix the pulling member in said hollow portion.

18. The tool according to claim 1, wherein said manipulator includes a hard pipe sheath and said sheath has an outer diameter larger than an outer diameter of a needle body of said penetration needle.

19. The tool according to claim 1, wherein said manipulator means includes a hard pipe sheath and each of said penetration needle and said sheath has a length longer than 150 mm.

20. The tool according to claim 1, wherein said manipulator includes a hard pipe sheath, and said pulling member includes a manipulating rod having a length at least 80 mm longer than a length of each of said penetration needle and said sheath.

21. The tool according to claim 1, further comprising a guide freely insertable into the hollow portion of said penetration needle.

22. The tool according to claim 21, wherein said guide is insulated at least on an outer circumference thereof.

23. The tool according to claim 21, wherein said guide includes a hard line member and an insulating member covering the hard line member.

24. A tool in combination with a pipe for manipulating tissue, comprising:
a pipe;
a manipulating rod adapted to be inserted into a body cavity of a patient through said pipe;
a connecting wire having a first end fixed to a front end of said manipulating rod; and
a stopper member adjacent said front end of said manipulating rod and fixed to a second end of said connecting wire, said stopper member being adapted to be held at a first position such that it is aligned with said manipulating rod in a straight line in an axial direction of the manipulating rod when the manipulating rod is inserted into the body cavity in said pipe, and said stopper member being adapted to be swung to a second position substantially perpendicular to the manipulating rod when the manipulating rod is projected outward from the body cavity, and said pipe and manipulating rod being adapted to permit the user to manipulate the stopper while inside the body cavity and to remove said pipe from over said manipulating rod while the stopper remains in the body cavity.

25. A method of manipulating tissue in a body cavity of a patient comprising:
a first step of sticking a penetration needle into the body cavity of the patient and further into tissue therein;
a second step of introducing pulling means into the tissue through a hollow portion of said penetration needle to hang up the tissue after said penetration needle is stuck therein;
a third step of pulling the penetration needle from the body cavity of the patient while leaving said pulling means in the body cavity;
a fourth step of inserting an outer portion of said pulling means, which is outside the body cavity of the patient, into a hollow portion of a manipulating means, guiding the manipulating means over the pulling means to insert the manipulating means into the body cavity of the patient, and positionally fixing the pulling means relative to the manipulating means; and a fifth step of manipulating said pulling means and said manipulating means to move the hung up tissue in a desired direction and hold the hung up tissue in a desired position.

26. The method according to claim 25, wherein said first step comprises applying a high frequency current to the penetration needle and sticking the penetration needle into the body cavity of the patient and further into the tissue therein while the high frequency current is being applied.

27. A method of manipulating tissue in a body cavity of a patient comprising:

a first step of sticking a penetration needle, which has a hollow portion, into the body cavity of the patient;

a second step of inserting guide means into the body cavity through the hollow portion of said penetration needle;

a third step of pressing tissue in the body cavity with a front end of said guide means to confirm a target portion of the tissue which is to be stuck by the penetration needle;

a fourth step of sticking said penetration needle into the target portion of the living tissue;

a fifth step of pulling said guide means outside the hollow portion of said penetration needle;

a sixth step of introducing pulling means into the living tissue in the body cavity through the hollow portion of said penetration needle after the needle is stuck into the target portion of the tissue in the body cavity;

a seventh step of pulling only the penetration needle outside the body cavity of the patient.

28. The method according to claim 27, further comprising:

an eighth step of inserting an outer portion of said pulling means, which is outside the body cavity of the patient, into a hollow portion of a manipulating means, guiding the manipulating means over the pulling means to insert the manipulating means into the body cavity of the patient, and positionally fixing the pulling means relative to the manipulating means; and a ninth step of manipulating said pulling means and said manipulating means to move the hung up tissue in a desired direction and hold the hung up tissue in a desired position.

\* \* \* \* \*